United States Patent
Yamashita et al.

(10) Patent No.: US 8,765,465 B2
(45) Date of Patent: Jul. 1, 2014

(54) EFFICIENT PRODUCTION AND USE OF HIGHLY CARDIOGENIC PROGENITORS AND CARDIOMYOCYTES FROM EMBRYONIC AND INDUCED PLURIPOTENT STEM CELLS

(75) Inventors: Jun Yamashita, Kyoto (JP); Peishi Yan, Kyoto (JP)

(73) Assignee: Kyoto University, Kyoto (JP)

( * ) Notice: Subject to any disclaimer, the term of this patent is extended or adjusted under 35 U.S.C. 154(b) by 940 days.

(21) Appl. No.: 12/452,531

(22) PCT Filed: Aug. 29, 2008

(86) PCT No.: PCT/JP2008/066033
§ 371 (c)(1),
(2), (4) Date: Jan. 7, 2010

(87) PCT Pub. No.: WO2009/118928
PCT Pub. Date: Oct. 1, 2009

(65) Prior Publication Data
US 2011/0104122 A1    May 5, 2011

Related U.S. Application Data

(60) Provisional application No. 61/064,777, filed on Mar. 26, 2008.

(51) Int. Cl.
*C12N 5/00* (2006.01)
*C12N 5/02* (2006.01)
(52) U.S. Cl.
USPC .......................... 435/325; 435/404; 435/405
(58) Field of Classification Search
None
See application file for complete search history.

(56) References Cited

FOREIGN PATENT DOCUMENTS

JP   2002-153281   5/2002
WO   2007/069666   6/2007

OTHER PUBLICATIONS

Narazaki et al., Circulation, vol. 118(5), pp. 498-506, Jul. 14, 2008.
Yan et al., Circulation Journal, vol. 72, Suppl. I, p. 75, Mar. 1, 2008.
Yamashita et al., FASEB J., vol. 19(11), pp. 1534-1536, 2005.
Yanagi et al., Stem Cells, vol. 25(11), pp. 2712-2719, 2007.
Sachinidis et al., Cell Physiol. Biochem., vol. 18(6), pp. 303-314, 2006.
Takahashi et al., Cell, vol. 126(4), pp. 663-676, Aug. 25, 2006.
Yu et al., Science, vol. 318, pp. 1917-1920, Nov. 20, 2007.
Takahashi et al., Cell, vol. 131, pp. 1-12, Nov. 20, 2007.
Yamashita et al., Circulation Journal, vol. 72, Suppl. I, p. 132, Mar. 1, 2008.
International Search Report that issued with respect to PCT/JP2008/066033, mailed Nov. 4, 2008.
Written Opinion that issued with respect to PCT/JP2008/066033, mailed Nov. 4, 2008.
Yamashita et al., "Prospective identification of cardiac progenitors by a novel single cell-based cardiomyocyte induction," *FASEB J.*, full text published online Jul. 20, 2005.
Japanese Office Action issued with respect to Japanese Patent App. No. 2010-507561, mailed Aug. 20, 2013.

*Primary Examiner* — Debbie K Ware
(74) *Attorney, Agent, or Firm* — Greenblum & Bernstein, P.L.C.

(57) ABSTRACT

This invention relates to a method for producing cardiomyocytes and/or cardiac progenitor cells, comprising culturing an induced pluripotent stem (iPS) cell or embryonic stem (ES) cell, which has been differentiated into a mesoderm cell, in the presence of cyclosporin-A.

16 Claims, 21 Drawing Sheets

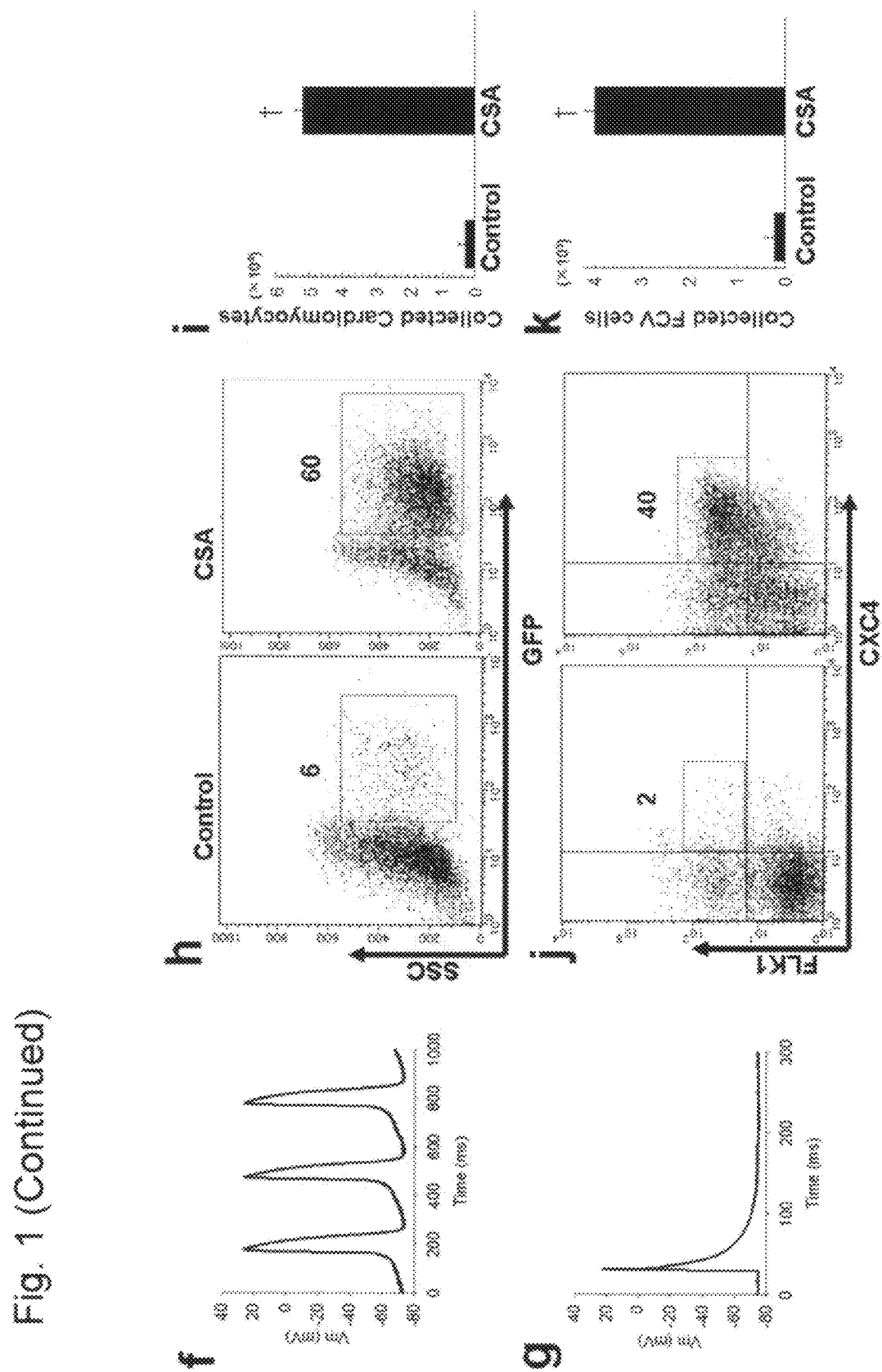

EFFICIENT PRODUCTION AND USE OF HIGHLY CARDIOGENIC PROGENITORS AND CARDIOMYOCYTES FROM EMBRYONIC AND INDUCED PLURIPOTENT STEM CELLS

PRIORITY OF THIS APPLICATION

This application is a National Stage Application of International Application No. PCT/JP2008/066033, filed Aug. 29, 2008, which claims priority to U.S. Provisional Application No. 61/064,777, filed Mar. 26, 2008. The entire disclosure of the priority application is considered as being part of this application and is expressly incorporated by reference herein in its entirety.

FIELD OF THE INVENTION

This invention relates to a method for producing cardiomyocytes and/or cardiac progenitor cells. More specifically, said method comprises culturing an induced pluripotent stem (iPS) cell or embryonic stem (ES) cell, which has been differentiated into a mesoderm cell, in the presence of cyclosporin-A.

BACKGROUND OF THE INVENTION

Recently, novel pluripotent stem cells that are different from embryonic stem (ES) cells but are ES-cell like, i.e., induced pluripotent stem (iPS) cells, were generated from adult somatic cells by transduction with genes encoding defined transcription factors (Takahashi, K. and Yamanaka, S., *Cell* 126, 663-676 (2006); Okita, K., Ichisaka, T. and Yamanaka, S., *Nature* 448, 313-317 (2007); Takahashi, K. et al., *Cell* 131, 861-872 (2007); Yu, J. et al., *Science* 318, 1917-1920 (2007)). Establishment of iPS cells from adult human tissue is facilitating clinical application of iPS cells through cell transplantation-based regenerative medicine and generation of patient-specific cellular models and drug discovery systems (Yamanaka, S., *Cell Stem Cell* 1, 39-49 (2007); Laflamme, M. A. and Murry, C. E., *Nat. Biotechnol.* 23, 845-856 (2005); Kovacic, J. C., et al., *Cell Stem Cell* 1, 628-633 (2007)).

As ES cells and iPS cells show almost similar overall features for growth, pluripotency, and differentiation (Takahashi, K. and Yamanaka, S., *Cell* 126, 663-676 (2006); Okita, K. et al., *Nature* 448, 313-317 (2007); Takahashi, K. et al., *Cell* 131, 861-872 (2007); Yu, J. et al., *Science* 318, 1917-1920 (2007); Narazaki, G, et al., *Circulation* 118, 498-506 (2008)), studies for ES cells may be utilized as scientific and technological basis for iPS cell research. Previously, we established a novel ES cell differentiation system that can reproduce the early process of cardiovascular development in vitro (Yamashita, J. et al., *Nature* 408, 92-96 (2000); Yamashita, J. K. et al., *FASEB J.* 19, 1534-1536 (2005); Yanagi, K. et al., *Stem Cells* 25, 2712-2719 (2007); Yurugi-Kobayashi, T. et al., *Arterioscler. Thromb. Vasc. Biol.* 26, 1977-1984 (2006); Kono. T. et al., *Arterioscler. Thromb. Vasc. Biol.* 26, 2070-2076 (2006); Hiraoka-Kanie, M. et al, *Biochem. Biophys. Res. Commun.* 351, 669-674 (2006)). Endothelial cells (ECs), mural cells (MCs; pericytes and vascular smooth muscle cells) (Yamashita, J. et al., *Nature* 408, 92-96 (2000)), and cardiomyocytes (Yamashita, J. K. et al., *FASEB J.* 19, 1534-1536 (2005)) are systematically induced from common mesodermal precursor, i.e., Flk1 (also designated as vascular endothelial growth factor receptor-2 (VEGFR2))-expressing cells. We also succeeded in identifying a cardiac progenitor population, FCV cells (Flk1$^+$/CXCR4$^+$/vascular endothelial cadherin$^-$ cell population) among the progeny of Flk1$^+$ mesoderm cells (Yamashita, J. K. et al., *FASEB J.* 19, 1534-1536 (2005)). Though FCV cells, which are only a small subset of Flk1$^+$ cell progeny, showed highly cardiac specific progenitor activity, efficient expanding method of FCV cells remain unknown. More recently, we succeeded in establishing a similar mouse iPS differentiation system for cardiovascular cells (Narazaki, G, et al., *Circulation* 118, 498-506 (2008)), enabling to examine the induction of FCV progenitor cells from iPS cells.

However, as for cardiomyocytes, iPS cell technologies, such as efficient ways to induce cardiomyocytes, identification and expansion of cardiac progenitors, and establishment of model systems for cardiac differentiation, have not been established.

An object of this invention is to provide a method for effectively induce cardiac progenitor cells and/or cardiomyocytes from ES cells or iPS cells.

Another object of this invention is to provide cardiac progenitor cells or cardiomyocytes produced by said method.

Another object of this invention is to provide a method for treating a subject with heart disease by using said cardiac progenitor cells or cardiomyocytes.

Another object of this invention is to provide a use of said cardiac progenitor cells or cardiomyocytes in manufacture of a medicament or transplant or implant for treatment of a heart disease.

Another object of this invention is to provide a method for screening for an agent capable of inducing cardiomyocytes and/or cardiac progenitor cells.

We have now found that addition of cyclosporin-A (CSA), an immunosuppressant, to Flk1$^+$ mesoderm cells potently induces cardiomyocytes through specific expansion of FCV cardiac progenitor population. We have further now found this simple method in the ES cell systems could be completely adapted for use in iPS cells, specifically that cardiac progenitors and cardiomyocytes could be effectively induced from Flk1$^+$ mesoderm cells derived from human or mouse iPS cells. This novel differentiation technology would broadly contribute to cardiac regeneration by providing cell sources, transplantation strategies, and drug discovery.

SUMMARY OF THE INVENTION

Thus, this invention is summarized as follows:

In the first aspect, this invention provides a method for producing cardiomyocytes and/or cardiac progenitor cells, comprising culturing an iPS cell or ES cell, which has been differentiated into a mesoderm cell, in the presence of cyclosporine-A.

In one embodiment, the mesoderm cell is Flk1-positive (Flk1$^+$).

In another embodiment, the cardiac progenitor cells have an ability to differentiate into myocardium, and more specifically the cardiac progenitor cells are a Flk1$^+$/CXCR4$^+$/vascular endothelial cadherin$^-$ cell population.

In still another embodiment, the cardiomyocytes or cardiac progenitor cells have an ability to integrate a myocardial tissue.

In another embodiment, the iPS cell or ES cell is from mammals including ungulates (e.g., cow, sheep, goat, pig, etc.), rodents (e.g., mouse, rat, hamster, etc.), primates (human, monkey, chimpanzee, etc.), and the like. Preferably, the mammals are human and mouse.

In another embodiment, the iPS cell is generated from a somatic cell of a mammal. The somatic cells are any cells other than germline cells, such as cells making up organs, tissues, etc. Examples of the somatic cells are liver cells, stomach cells, or skin cells.

In another embodiment, the iPS cells can be generated from a somatic cell of a mammal by transduction with genes encoding transcription factors of at least Oct and Sox family members. The transcription factors may further comprise a transcription factor of a Klf family member, or transcription factors of a Klf family member and a Myc family member. Preferably, the Oct family member can include Oct3/4; the Sox2 family member can include Sox2; the Klf family member includes Klf4; and the Myc family member can include c-Myc.

In the second aspect, this invention also provides a method for screening candidate agents for an agent capable of inducing cardiomyocytes and/or cardiac progenitor cells, comprising culturing an iPS cell, which has been differentiated into a mesoderm cell, in the presence of a candidate agent, and selecting said agent based on the formation of beating colonies and/or Flk1$^+$/CXCR4$^+$/vascular endothelial cadherin$^-$ cells.

In the third aspect, this invention further provides cardiomyocytes, cardiac progenitor cells, or mixtures thereof produced by the method as defined above.

In the fourth aspect, this invention further provides a method for treating a subject with heart disease, comprising transplanting the cardiomyocytes, cardiac progenitor cells, or mixtures thereof as defined above, to the heart of the subject. The subject includes mammals as defined above, preferably a human. The heart disease includes, but is not limited to, heart failures including myocardial infarction and cardiomyopathy.

In the fifth aspect, this invention further provides use of the cardiomyocytes, cardiac progenitor cells, or mixtures thereof as defined above, in manufacture of a medicament or transplant or implant for treating a subject with heart disease. The subject and the heart disease are as defined above.

BRIEF DESCRIPTION OF THE DRAWINGS

FIGS. 1a-i. Cardiomyocyte induction from Flk1$^+$ mesoderm by CSA (experiment 1). a, b. Gross appearance of cardiomyocyte induction by CSA. Left panels: control. Right panels: CSA treatment. Scale bars=400 µm. FIG. 1a. Appearance of beating colony. Arrows indicate beating colonies. Arrow heads surround large beating area. FIG. 1b. Cardiomyocyte stained with cTnT (brown). FIG. 1c. Quantitative evaluation of cardiomyocyte induction by fluorescent intensity of cTnT staining. Relative fluorescent intensity is indicated (n=9, †p<0.001 vs control). FIGS. 1d, e. Appearance of isolated cardiomyocytes. d. cTnT (red) and DAPI (blue) staining. Scale bar=50 µm. e. Actinin (red) staining. Right panel shows higher magnification of boxed area. Apparent sarcomere structures are observed. Scale bar=25 µm. FIGS. 1f, g. Action potentials of induced cardiomyocytes. FIG. 1f. Cell with pacemaker potential and spontaneous beating. FIG. 1g. Quiescent ventricular type cell. FIG. 1h. FACS analysis for GFP$^+$ cardiomyocyte induction by CSA. Left panel: control. Right panel: CSA treatment. X axis: alpha MHC promoter-driven GFP. Y axis: side scatter. All Flk1$^+$ cell-derived population was analyzed. Percentages of GFP$^+$ cardiomyocytes are indicated. FIG. 1i. Yield of purified cardiomyocytes. Cell number of obtained GFP$^+$ cardiomyocytes from 10$^4$ Flk1$^+$ cells (n=12, †p<0.001 vs control). FIGS. 1j, k. Induction of FCV progenitor cells from Flk1$^+$ mesoderm (experiment 3). FIG. 1j. FACS analysis for cardiac progenitor induction by CSA. X axis: Flk1. Y axis: CXCR4. Percentages of FCV cells (double positive population) are indicated. FIG. 1k. Yield of purified cardiac progenitor cells. Cell number of obtained FCV progenitor cells from 10$^4$ Flk1$^+$ cells (n=12, †p<0.001 vs control). FIGS. 1l, m. Representative data of FCV cell transplantation (4×10$^5$ cells) to rat myocardial infarction model. Double immunostaining for GFP and cTnT. Upper panels: GFP (donor cell-derived cardiomyocytes, green) and DAPI (blue). Lower panels: cTnT (pan-cardiomyocytes, red) and DAPI. FIG. 1l. Gross appearance of transplanted cells contributing to repair of infarct area. Scale bars=400 µm. FIG. 1m. Higher magnification views of boxed area. Arrowheads show cTnT$^+$/GFP$^-$ endogenous cardiomyocytes. Scale bars=50 µm. FIG. 1n. Reciprocal appearance of ECs and cardiomyocytes by CSA treatment (experiment 1). Double immunostaining for CD31 (pan-ECs; green) and cTnT (red). Upper panel: control. Lower panel: CSA treatment. Scale bars=400 µm.

FIGS. 2a, b. Cardiomyocyte induction from mouse iPS cell-derived Flk1$^+$ mesoderm by CSA (experiment 1). FIG. 2a. Gross appearance of cardiomyocyte induction by CSA. cTnT staining (red). Left panel: control. Right panel: CSA treatment. Scale bars=400 µm. FIG. 2b. Quantitative evaluation of cardiomyocyte induction by fluorescent intensity of cTnT staining. Relative fluorescent intensity is indicated (n=4, †p<0.001 vs control). FIG. 2c. FACS analysis for cardiac progenitor induction from mouse iPS cells by CSA (experiment 3). X axis: Flk1. Y axis: CXCR4. Percentages of FCV cells (double positive population) are indicated. FIGS. 2d-i. Cardiomyocyte induction from human iPS cells. Human iPS cells were co-cultured with END-2 cells to induce cardiomyocytes. FIG. 2d. Gross appearance of beating colonies from human iPS cells. Beating colonies are indicated by arrowheads. Scare bar=400 µm. FIG. 2e. cTnT staining of beating colonies on END2 cells. Left panel: phase contrast image. Right panel: human cTnT staining (green). Scale bars=100 µm. FIG. 2f. Actinin staining of dissociated beating colonies. Actinin (red) and DAPI (blue). Right panel shows higher magnification of boxed area. Apparent sarcomere structures are observed. Scale bar=25 µm. FIG. 2g. Ca$^{++}$ transient in dissociated beating colonies. Cytoplasmic Ca$^{++}$ change was monitored with fluo-8. Left panel: a transmission image of fluo-8 loaded iPS colony. Middle and left panels: Fluo-8 images at the end (A) and the peak (B) of the fluorescence change. Scale bar=50 µm. Lower panel: Time course of fluo-8 intensity change. The intensity was measured at the periphery (1), the entire colony (2) and the center (3) (ROIs shown in middle panel). Ratios (F1/F0) of the intensity to the one at the beginning of recording (F0) are indicated. Note that Ca transient is well synchronized within the colony. FIGS. 2h, i. Cardiomyocyte induction from human iPS cells by CSA. FIG. 2h. Representative gross appearance of human iPS cell-derived beating colonies in 12 well dish. Left panel: control. Right panel: CSA treatment from differentiation day8. Red arrowheads: beating colonies. FIG. 2i. Percentages of beating colonies in total appeared human iPS cell-derived colonies on END-2 cells at differentiation day 12 (n=8, †p<0.001).

FIGS. 3A, B. Representative data of cell transplantation. Contribution of transplanted cells as cardiomyocytes was evaluated by immunostaining of GFP (brown). Scale bars=400 µm. Inset shows higher magnification of boxed area. Scale bars=100 µm. FIG. 3A. GFP$^+$ cell injection (4×10$^5$ cells). FIG. 3B. FCV progenitor cell injection ($4\times10^5$ cells). FIG. 3C. Double immunostaining for Cx43 (green) and cTnT (red). Cx43 was observed among adjacent cTnT$^+$ cardiomyocytes (arrowheads). Scale bars=100 μm. FIG. 3D. Estimated area of regenerated cardiomyocytes (n=3, **p<0.01 vs GFP$^+$ cell injection). FIG. 3E. Estimated volume of regenerated cardiomyocytes (n=3, †p<0.001, vs GFP$^+$ cell injection).

In this experimental system, cells representing four different differentiation stages are sequentially induced, that is, undifferentiated ES cells, Flk1$^+$ mesoderm cells, FCV cardiac progenitor cells, and cardiomyocytes. Undifferentiated ES cells were cultured on OP9 cells or type IV collagen (Col. IV)-coated dishes (ES-d0) for 96-108 h in differentiation medium (see Methods) to induce differentiation to Flk1$^+$ cells. Flk1$^+$/E-cadherin$^-$ mesoderm cells obtained by FACS were plated onto OP9 stroma cells to induce further differentiation to cardiomyocytes (designated as Flk-d0). FCV cells appeared at Flk-d2 as Flk1$^+$/CXCR4$^+$/vascular endothelial cadherin$^-$ population. Beating colonies started to be observed by Flk-d4. Appearance of alpha-MHC promoter-driven GFP$^+$ cardiomyocytes were evaluated and collected at Flk-d6. Experiment 1: differentiation from mesoderm to cardiomyocytes. CSA was added to purified Flk1$^+$ mesoderm cells at Flk-d0, and cardiomyocyte appearance was estimated at Flk-d6. Experiment 2: differentiation from undifferentiated ES cells to mesoderm. CSA was added to undifferentiated ES cells at ES-d0, and mesoderm induction was estimated as Flk1$^+$ cell appearance by FACS at ES-d4. Experiment 3: differentiation from mesoderm to cardiac progenitors. CSA was added to Flk1$^+$ cells at Flk-d0, and appearance of FCV cardiac progenitor cells was estimated by FACS at Flk-d2. Experiment 4: differentiation from cardiac progenitors to cardiomyocytes. CSA was added to purified FCV progenitor cells at Flk-d2, and appearance of cardiomyocytes was estimated at Flk-d6. Experiment 5: mesoderm-specific effects of CSA on differentiation of cardiomyocytes. CSA (or other reagents) was added only from Flk-d0 to d2, and appearance of cardiomyocytes was estimated at Flk-d6. Purified FCV cells at Flk-d2 were transplanted to chronic-stage rat myocardial infarction model.

Figure 5:
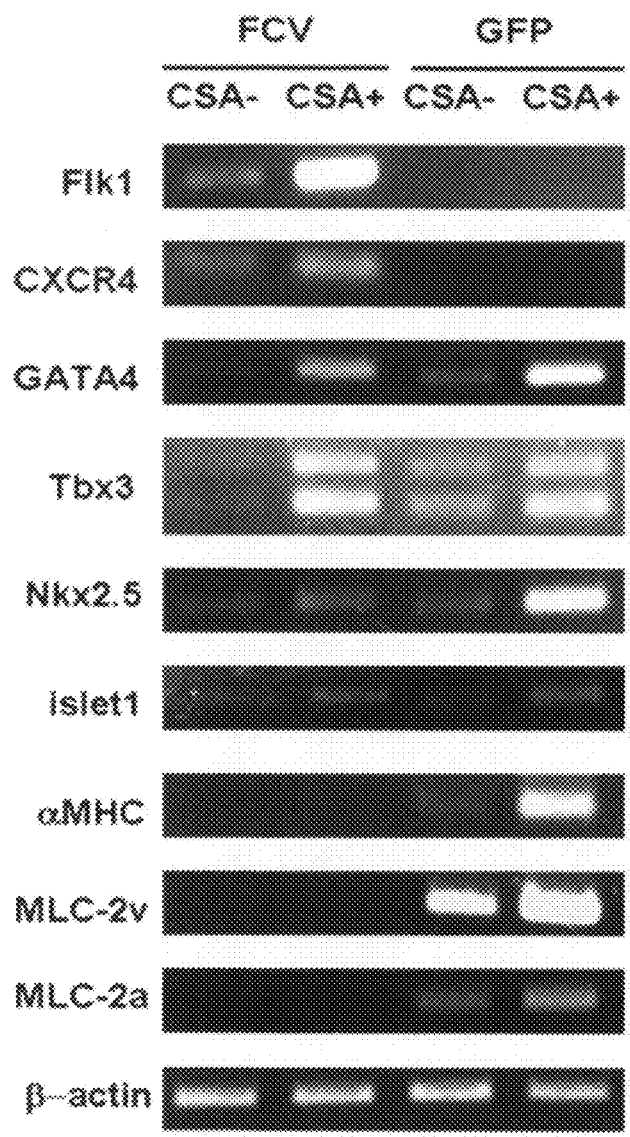

FIG. 5: RT-PCR analysis for cardiac markers of mouse ES cells in cardiomyocyte differentiation.

mRNA expressions in purified FCV progenitor cells or GFP$^+$ cardiomyocytes induce in the absence (CSA−) or presence (CSA+) of CSA.

Figure 6:
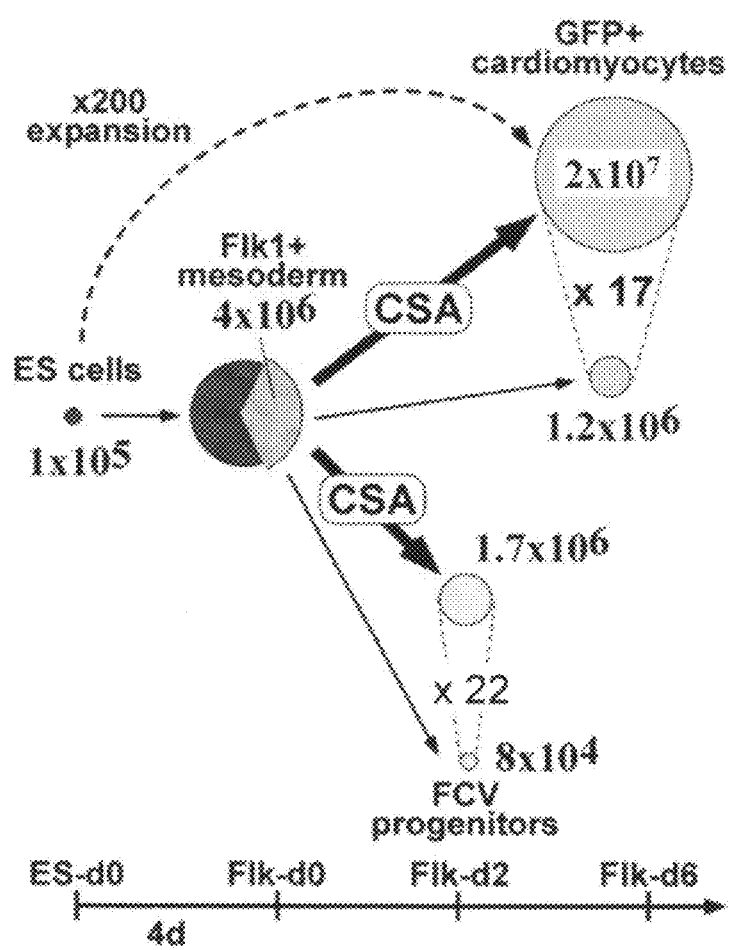

FIG. 6: Induction efficiency of cardiac cells from ES cells in this system.

Figure 1:
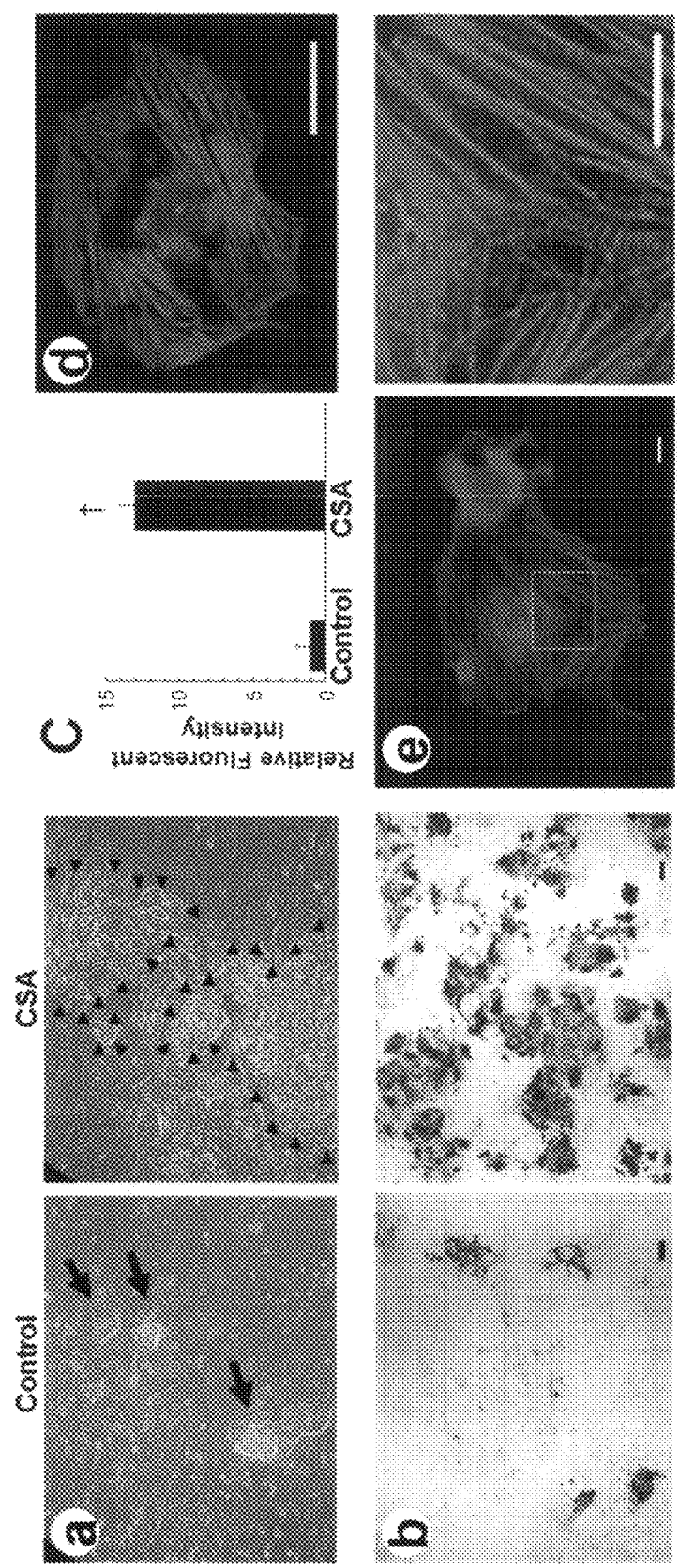
FIG. 1: Induction of cardiomyocytes and cardiac progenitors from ES cells by CSA treatment.
Figure 1:
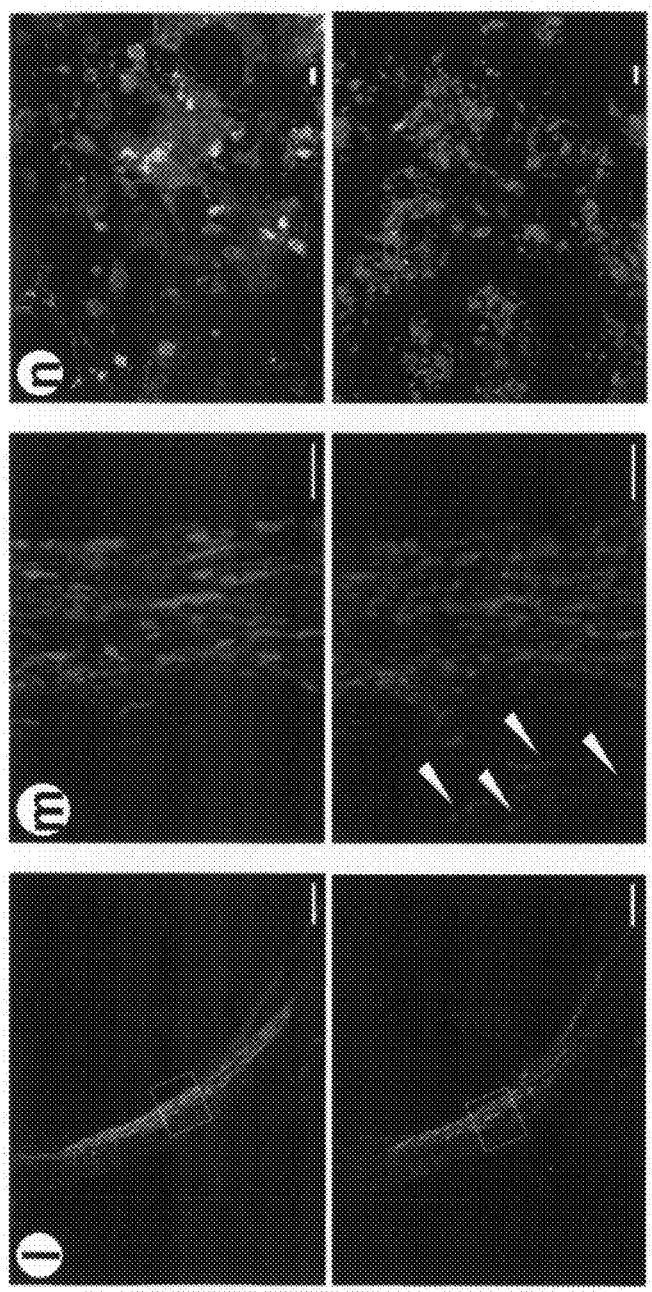

When starting the differentiation from $1\times10^5$ undifferentiated ES cells, total cell number is increased approximately 100-150 times (to $1$-$1.5\times10^7$ cells) during the first 4 days of mesoderm differentiation. Approximately 30-40% of total cells become Flk1$^+$ mesoderm cells (approximately $4\times10^6$ cells). After 6 days culture of purified Flk1$^+$ cells on OP9 cells (Flk-d6), approximately $1.2\times10^6$ of cardiomyocytes are obtained from $4\times10^6$ of Flk1$^+$ cells with our conventional method (FIG. 1i). CSA treatment enhances cardiomyocyte induction by approximately 17 times, resulting in $2\times10^7$ cardiomyocytes from $4\times10^6$ Flk1$^+$ cells (FIG. 1j). Approximately 200 cardiomyocytes can be induced from one ES cell after the CSA enhancement. On the other hand, only $8\times10^4$ FCV progenitor cells can be induced from $4\times10^6$ of Flk1$^+$ cells at Flk-d2 with our conventional method. CSA treatment enhances FCV progenitor induction approximately 22 times, resulting in $1.7\times10^6$ FCV cells from $4\times10^6$ Flk1$^+$ cells (FIG. 1k).

Figure 7:
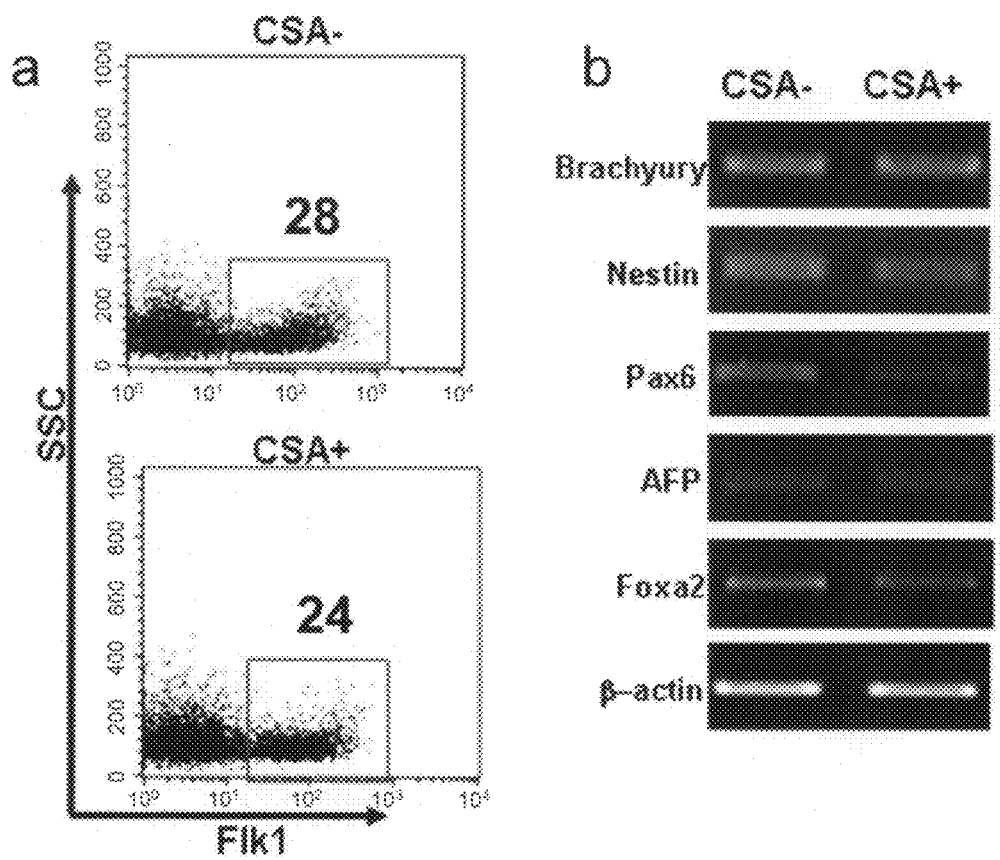

FIG. 7: Effect of CSA on early ES cell differentiation.

Effects of CSA on early differentiation from undifferentiated ES cells (experiment 2). FIG. 7a. FACS analysis for Flk1 at ES-d4 in the absence (CSA−) or presence (CSA+) of CSA. FIG. 7b. mRNA expressions for mesoendoderm marker, brachyury, ectoderm markers, Nestin and Pax6, and endoderm markers, AFP and Foxa2 at ES-d4.

Figure 8:
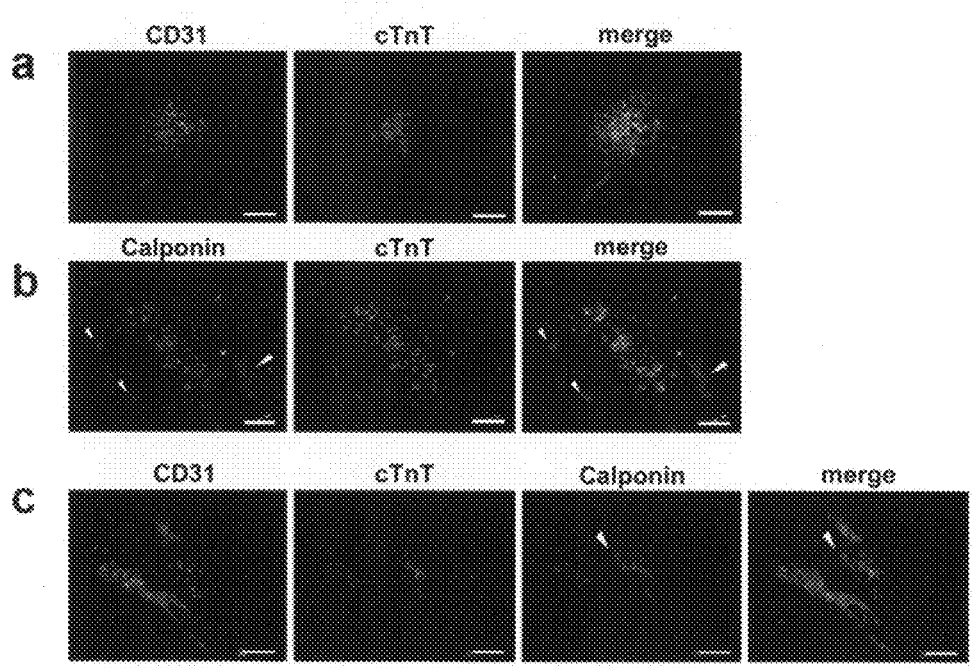

FIG. 8: Colonies from single FCV cell culture on OP9.

Triple staining of CD31 (pan-ECs, green), cTnT (pan-cardiomyocytes (CM), red), and calponin (cardiomyocytes and mural cells (MC), blue) together with DAPI (gray) for single FCV cell-derived colonies at Flk-d6. FIG. 8a. EC/CM colony. FIG. 8b. CM/MC colony. Arrowheads show calponin+/cTnT− MCs. FIG. 8c. Triple positive colony. Arrowhead shows calponin+/cTnT− MC. Scale bars=100 μm.

Figure 9:
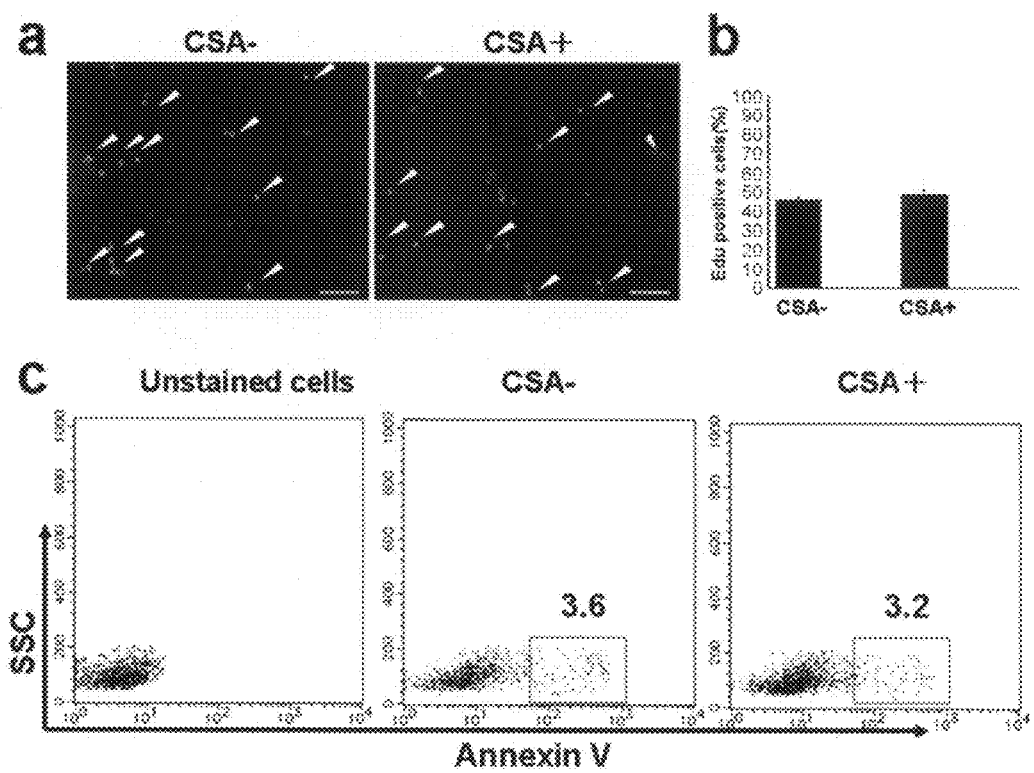

FIG. 9: Effects of CSA on proliferation or apoptosis of FCV cells.

FIGS. 9a, b. EdU incorporation. EdU-treated FCV cells were purified by FACS and plated onto glass slides by cytocentrifugation. FIG. 9a. Double staining for EdU (green) and DAPI (blue). Left panel: control (CSA−). Right panel: CSA treatment (CSA+). EdU$^+$ nuclei are indicated by arrowheads. Scale bar=100 μm. FIG. 9b. Quantitative evaluation of EdU$^+$ FCV cells. Percentages of EdU$^+$ cells in total cells are indicated. (200 nuclei each, n=3). FIG. 9c. FACS analysis for annexin V expression. Gated FCV cell populations are shown. Percentages of apoptotic cells (annexin V$^+$, red box) are indicated.

Figure 10:
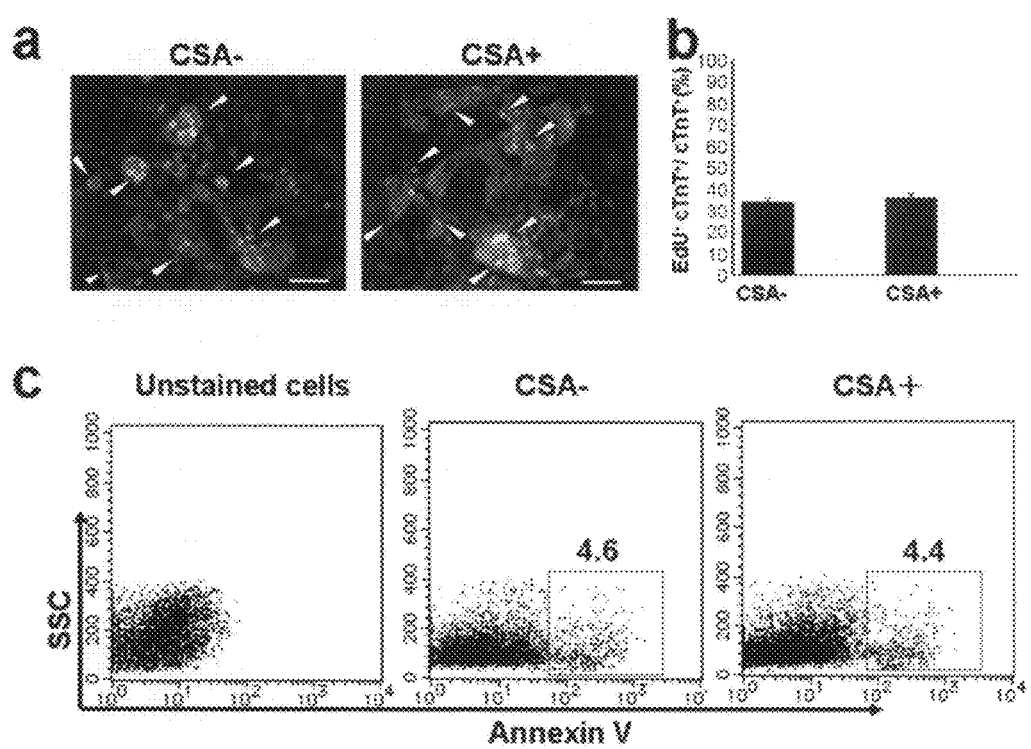

FIG. 10: Effects of CSA on proliferation or apoptosis of cardiomyocytes.

FIGS. 10a, b. EdU incorporation in cardiomyocytes at Flk-d3. FIG. 10a. Triple staining for cTnT (red), EdU (green) and DAPI (blue). Left panel: control (CSA−). Right panel: CSA treatment (CSA+). EdU$^+$/cTnT$^+$ cardiomyocytes are indicated by arrowheads. Scale bar=100 μm. FIG. 10b. Quantitative evaluation of EdU$^+$ cardiomyocytes. Percentages of EdU$^+$ cardiomyocytes in total cardiomyocytes are indicated. (200 nuclei each, n=3). FIG. 10c. FACS analysis for annexin V expression at Flk-d6. Gated GFP$^+$ cardiomyocytes populations are shown. Percentages of apoptotic cells (annexin V$^+$, red box) are indicated.

Figure 11:
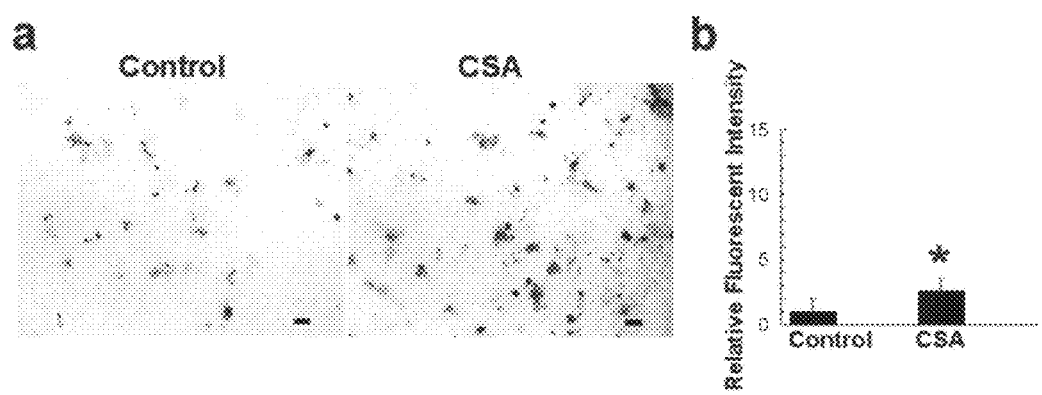

FIG. 11: Effect of CSA on FCV cell differentiation to cardiomyocytes.

FIGS. 11a, b. Cardiomyocyte induction from purified FCV cells by CSA (experiment 4). FIG. 11a. Gross appearance of cardiomyocytes stained with cTnT (brown). Left panel: control. Right panel: CSA treatment. Scale bars=400 μm. FIG. 11b. Quantitative evaluation of cardiomyocyte induction by fluorescent intensity of cTnT staining. Relative fluorescent intensity is indicated (n=3, *p<0.05 vs control).

Figure 12:
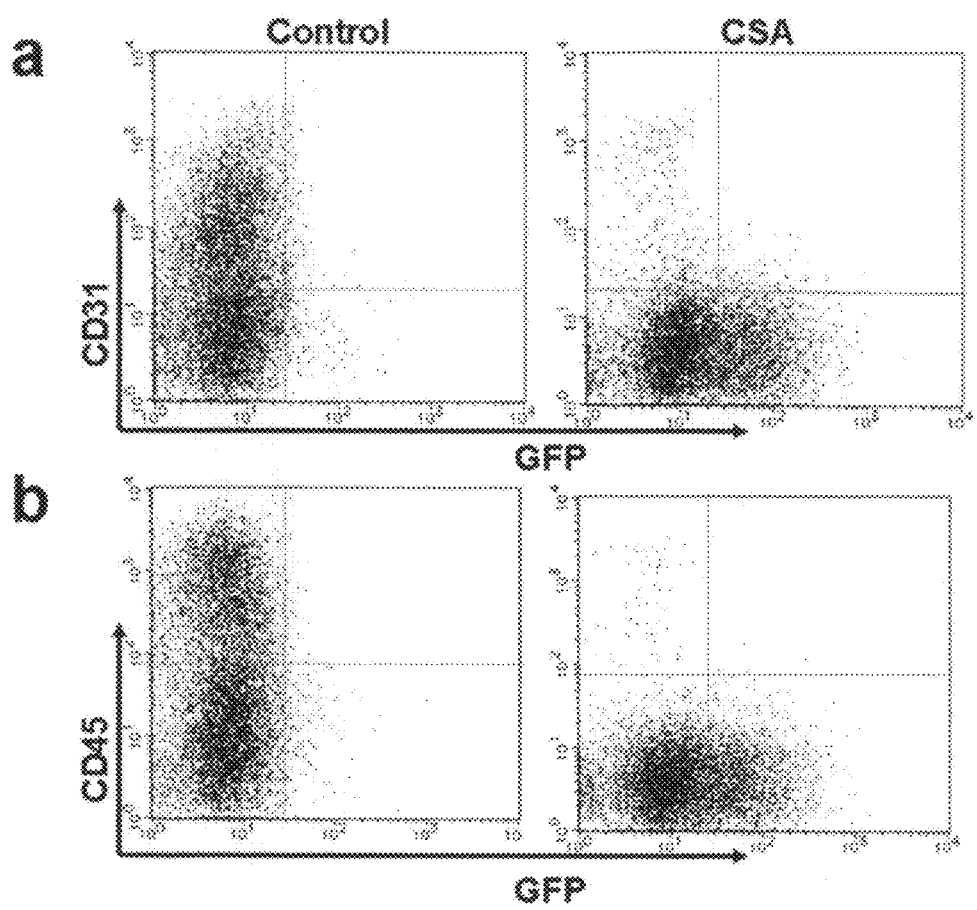

FIG. 12: Reciprocal appearance of ECs or blood cells with cardiomyocytes by CSA treatment.

FACS analysis at Flk-d6 (experiment 1). Left panel: control. Right panel: CSA treatment. X axis: alpha MHC promoter-driven GFP (cardiomyocytes). Y axis: CD31 (pan-ECs)(a), CD45 (pan-white blood cells)(b). All Flk1$^+$ cell-derived population was analyzed.

Figure 13:
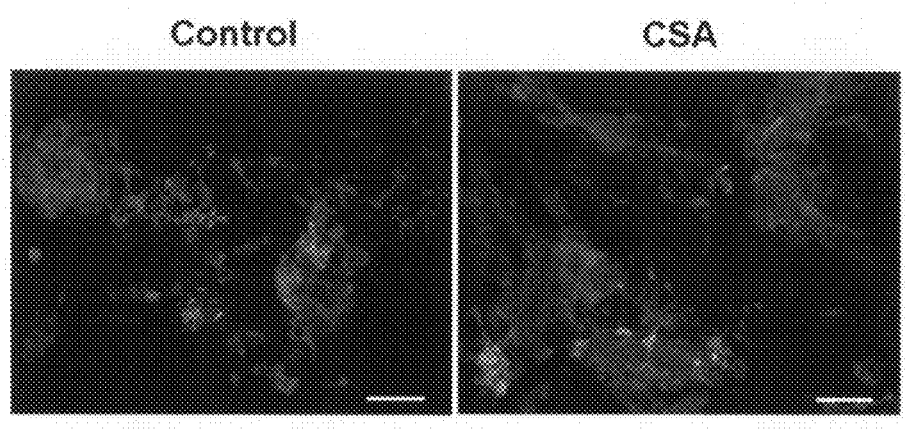

FIG. 13: Mesoderm-specific effect of CSA on EC and cardiomyocyte differentiation.

Cardiomyocyte and EC induction from Flk1$^+$ cells by mesoderm-specific treatment of CSA (experiment 5). Double immunostaining for CD31 (green) and cTnT (red) at Flk-d6. Left panel: control. Right panel: CSA treatment. Scar bars=100 μm. Note that increase in cTnT$^+$ cardiomyocytes and reciprocal decrease in CD31$^+$ ECs are induced by mesodermal treatment of CSA.

Figure 14:
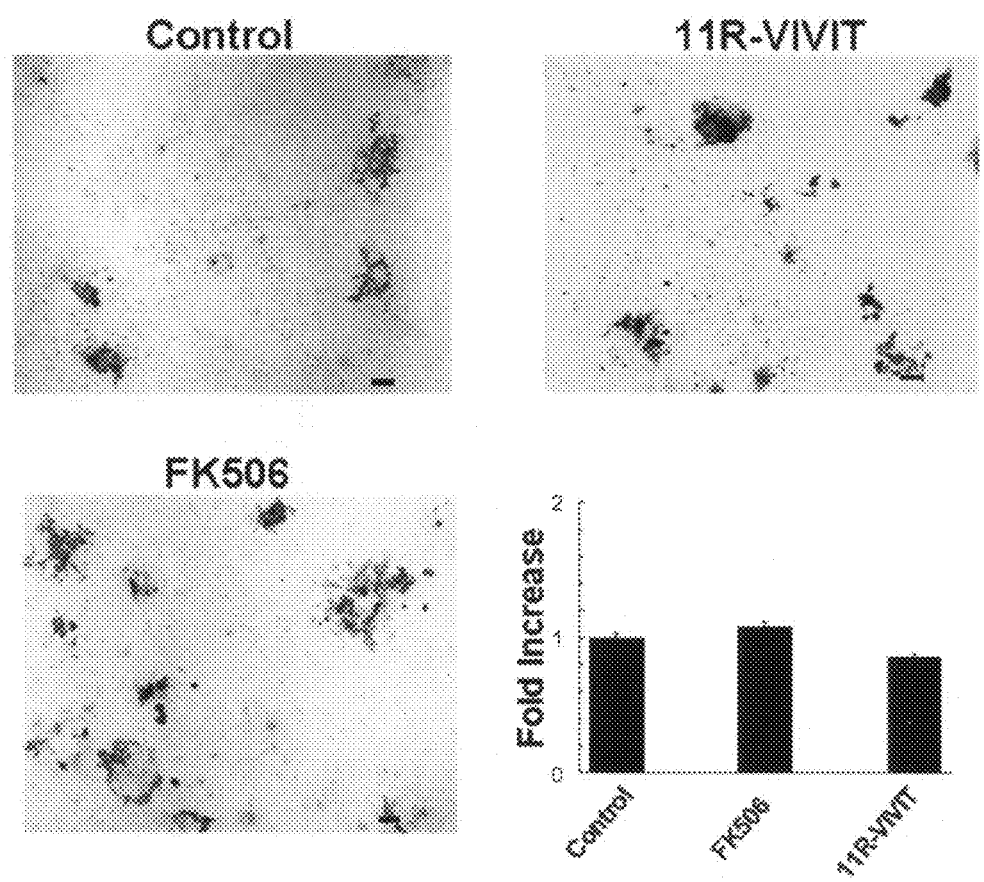

FIG. 14: Effects of FK506 and NF-AT inhibitor on cardiomyocyte differentiation.

Cardiomyocyte induction from Flk1+ cells by CSA (experiment 1). Photos: Gross appearance of cardiomyocytes stained with cTnT (brown), treated with vehicle (control), FK506, or a NF-AT inhibitor, 11R-VIVIT. Scale bars=400 μm. Bar graph: Quantitative evaluation of cardiomyocyte induction by fluorescent intensity of cTnT staining. Relative fluorescent intensity is indicated (n=3).

Figure 15:
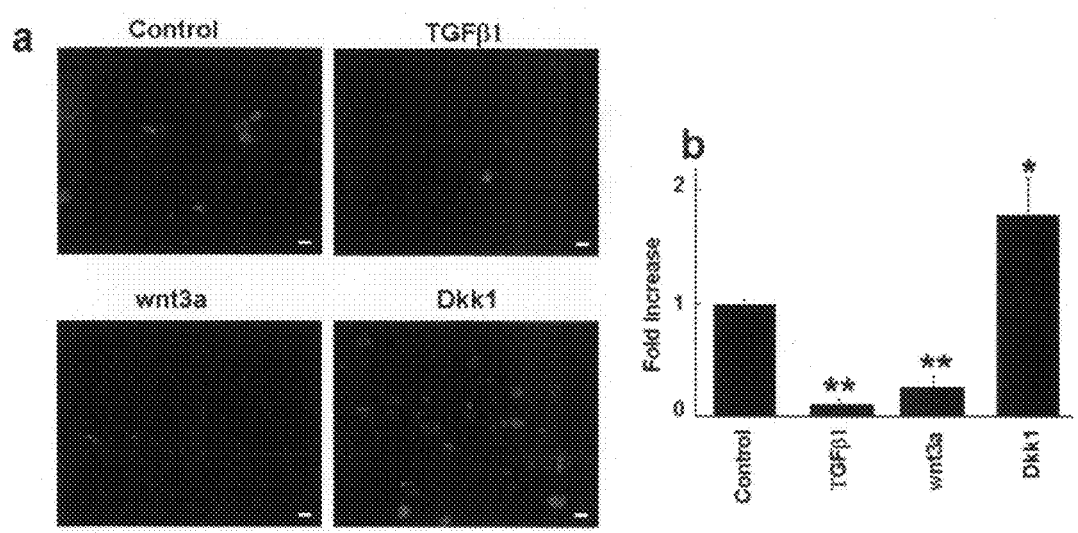

FIG. 15: Mesoderm-specific effects of TGF-β, wnt3a and Dkk1 on cardiomyocyte differentiation.

Figure 4:
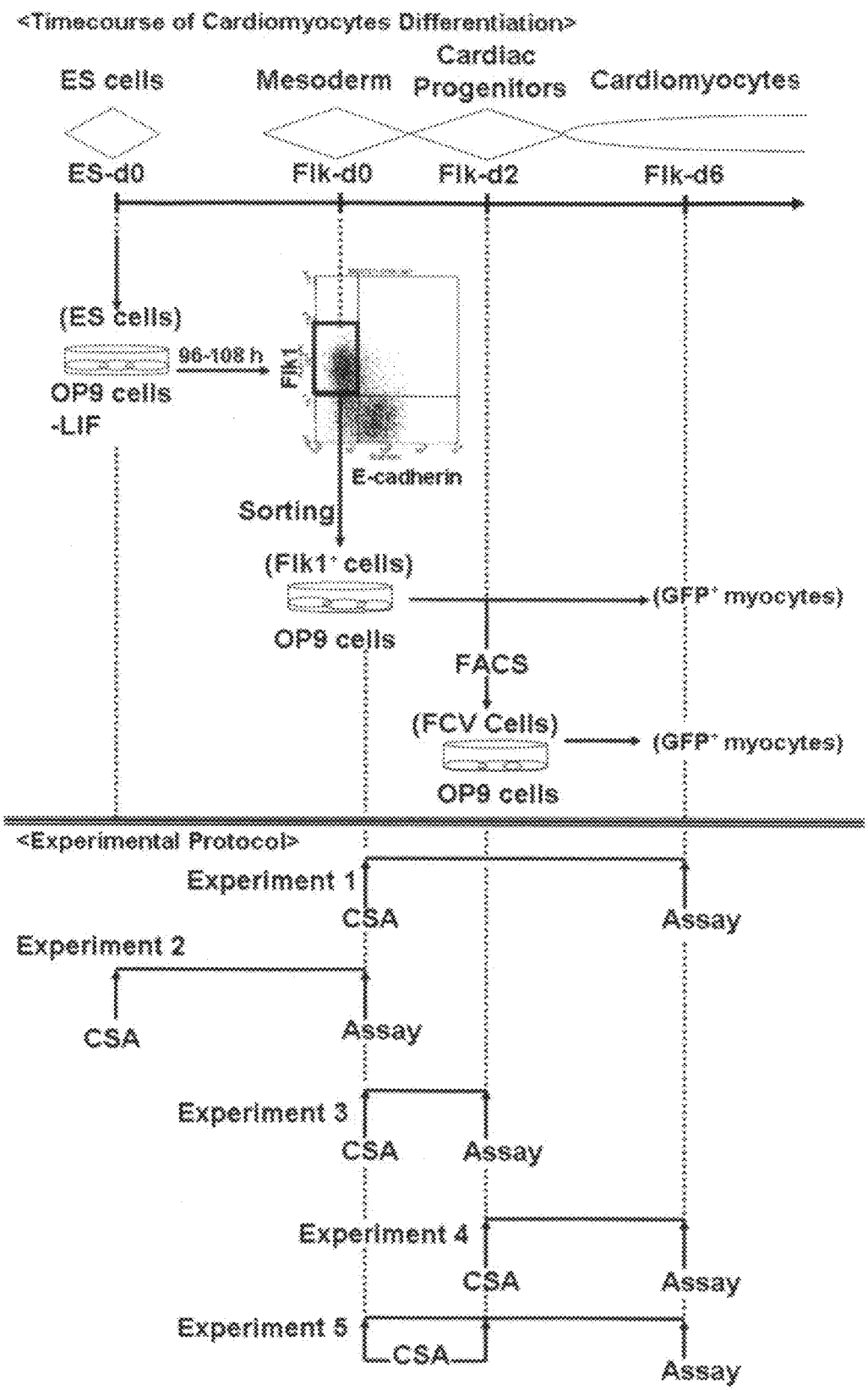
FIG. 4: Procedure and time course of cardiomyocyte differentiation.

Cardiomyocyte induction from Flk1+ cells by mesoderm-specific treatment of indicated factors (experiment 5 in FIG. 4). a. Gross appearance of cardiomyocytes stained with cTnT (red). Scale bars=400 μm. b. Quantitative evaluation of cardiomyocyte induction by fluorescent intensity of cTnT staining. Relative fluorescent intensities are indicated (n=3, *p<0.05, **p<0.01 vs control).

Figure 16:
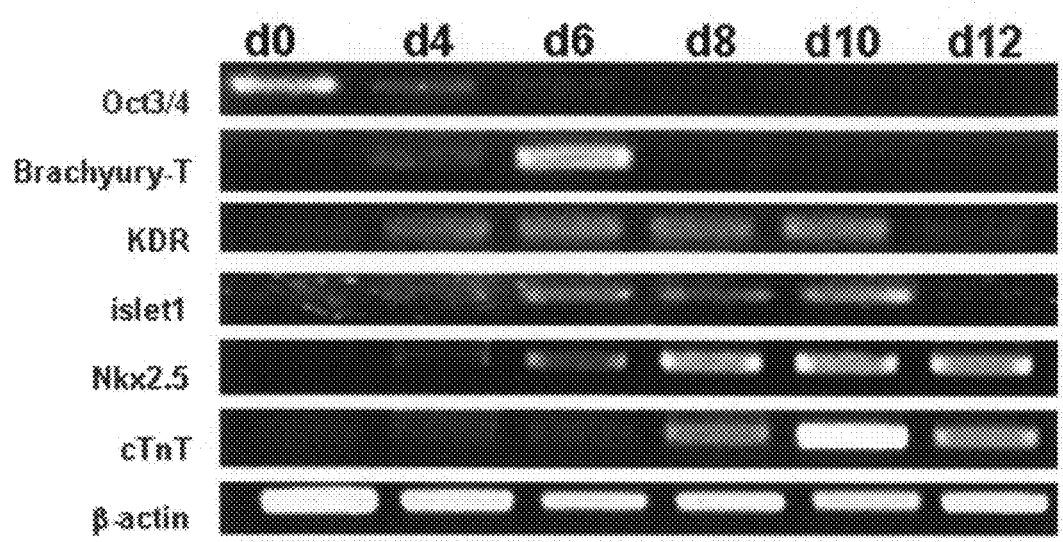

FIG. 16: RT-PCR analysis for differentiation markers during cardiomyocyte differentiation of human iPS cells.

mRNA expression of various genes during human iPS cell culture on END2 cells (from differentiation day 0 to day 12). Gene expression pattern largely reflected human iPS cell differentiation to cardiomyocytes. Undifferentiated cell marker, Oct3/4 was decreased after differentiation, and mesoderm/cardiac progenitor marker, islet1 was observed from day 6. Some of mRNA expressions preceded appearance of proteins or cellular phenotypes by several days. That is, whereas VEGFR2+ mesoderm cells appeared from human ES cells approximately 8 days after the differentiation (Sone, M. et al., Arterioscler. Thromb. Vasc. Biol. 27, 2127-2134 (2007)), a mesoendoderm marker, brachyury-T, and a mesoderm marker, KDR (VEGFR2), appeared from differentiation day 4. cTnT became apparent from day 8, though the first beating colonies appeared later than day 10.

Figure 17:
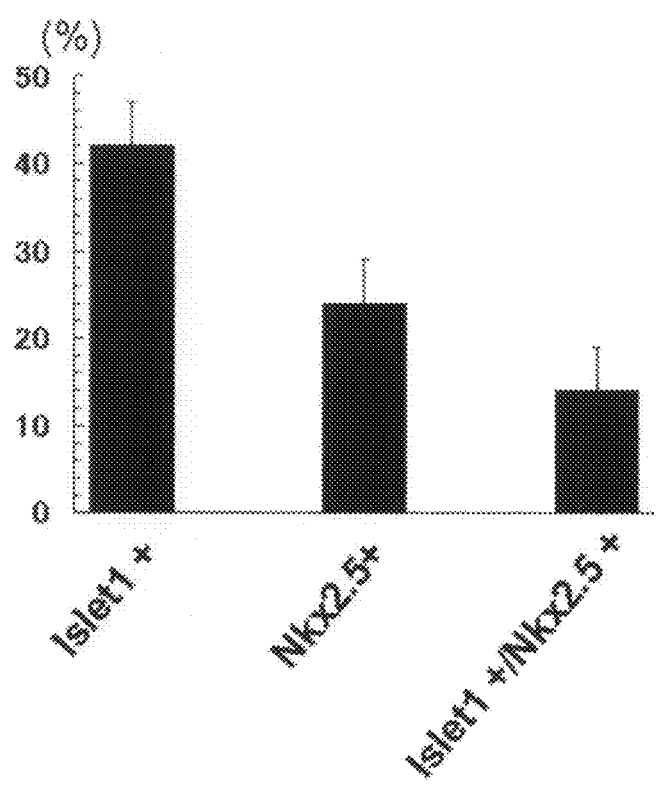

FIG. 17: Islet1 and Nkx2.5 expression in FCV progenitor cells.

Quantitative evaluation of islet1 and/or Nkx2.5 expressing cells in purified FCV cells. FCV cells were purified by FACS and plated onto glass slides by cytocentrifugation, and double stained with anti-islet1 and Nkx2.5 antibodies. Bar graph shows percentages of islet1 and/or Nkx2.5 positive cells in total FCV cells are indicated. (1000 cells each, n=3).

DETAILED DESCRIPTION OF THE INVENTION

Definitions

All terms used herein have their ordinary meanings to those of skill in the art unless indicated otherwise. The following terms have the following meanings.

As used herein, the term "cardiomyocyte" means a cell of the cardiac muscle which makes up the wall of the heart and has a property of self-beating.

The term "cardiac progenitor cell" as used herein means a progenitor of said cardiomyocyte. This cell has an ability to give rise to cardiomyocytes, which form the beating muscle and the electrically conductive tissue of the heart, and to vascular smooth muscle cells.

The term "embryonic stem cell" or "ES cell" as used herein means a pluripotent cell from the inner cell mass present within the blastocyst which is an early stage embryo of an animal. The ES cell has an ability to differentiate into any tissue of the body of an animal (Evans, M. J. and Kaufman, M. H., Nature 292, 154-156 (1981)). When a transformed ES cell is returned back to the blastcyst which is then transplanted into the uterus of a surrogate mother, chimeric transgenic animals can be created.

The term "induced pluripotent cell" or "iPS cell" as used herein means a cell with pluripotency derived artificially by nuclear reprogramming of differentiated cells, not oocytes, embryos or ES cells. This iPS cell can be induced from a somatic cell of a mammalian by its transduction with genes coding for three or four transcription factors as described by Takahashi, K. and Yamanaka, S. (Cell 126, 663-676 (2006)), Takahashi, K. et al. (Cell 131, 861-872 (2007)), or Yu, J. et al. (Science 318, 1917-1920 (2007)).

The term "Flk1" as used herein refers to vascular endothelial growth factor receptor 2 (VEGFR2).

The term "Flk1+/CXCR4+" as used herein means a biomarker pair for identifying ES cell progeny significantly enriched with Mesp-1, GATA-4, and Tbx5, indicative of pre-cardiac mesoderm. This biomarker pair can be used to predict the emergence of cardiogenic specification within a pluripotent stem cell pool, enabling targeted selection of cardiopoietic lineage (Nelson et al., Stem Cells 26, 1464-1473 (2008))

The term "transduction" as used herein means a process in which a foreign DNA is introduced into a cell using a vector such as viral vector, plasmid vector, or the like, whereby the cell contains the foreign DNA.

The term "transplantation" as used herein means transplanting a cell implant or transplant, which comprises cardiomyocyte, cardiac progenitor cells, or mixtures thereof, at an infracted or lesion site(s) of the heart of an animal.

The term "cyclosporine-A" or "CSA" as used herein refers to an immunosuppressant, which is normally used to prevent the rejection in a patient after transplantation of a solid organ or bone marrow because this compound has an ability to inhibit the activity of T cells. The CSA is available from Novartis (Basel, Switzerland) for example.

As used herein, the term "animal", "subject" or "patient" means mammals including primates, rodents, and ungulates, preferably humans.

Description of the Invention

1. Generation of Cardiomyocytes and/or Cardiac Progenitor Cells from ES Cells or iPS Cells This invention provides a method for producing cardiomyocytes and/or cardiac progenitor cells, comprising culturing an iPS cell or ES cell, which has been differentiated into a mesoderm cell, in the presence of cyclosporine-A (referred to as "CSA").

The phrase "an iPS cell or ES cell, which has been differentiated into a mesoderm cell" means that these cells are at the stage differentiated into mesoderm cells (i.e., mesoderm to early cardiac lineage), preferably Flk1+ (kinase insert domain protein receptor, also known as Kdr) cells. According to this invention, when CSA is added to the culture of iPS cells or ES cells at the mesoderm cell stage, they are more efficiently differentiated into cardiomyocytes and/or cardiac progenitor cells as compared with the conventional methods.

Until now, it was known to derive cardiomyocytes, cardiovascular cells, or cardiovascular progenitor cells from ES cells and iPS cells, using inducers comprising activin A and bone morphogenetic protein 4 (BMP4) (Takahasi, K. et al., Cell 131, 861-872 (2007); Laflamme, M. A. et al., Nat. Biotechnol. 25, 1015-1024 (2007); Yang, L. et al., Nature 453, 524-528 (2008)). However, the induction of cardiomyocytes and/or cardiac progenitor cells from ES cells or iPS cells by CSA, has now first been found by us.

We will describe below in more detail the generation of cardiomyocytes and/or cardiac progenitor cells from ES cells or iPS cells as starting cells.

1.1 Preparation of ES Cells

In this invention, any ES cells can be used as starting cells to derive cardiomyocytes and/or cardiac progenitor cells. As used herein, the term "cardiomyocytes and/or cardiac progenitor cells" is intended to include cardiomyocytes, cardiac progenitor cells, or mixtures or populations thereof.

The usable ES cells include mammalian ES cells, such as ES cells from primates, rodents, ungulates, etc., wherein the primates include human, monkey, chimpanzee, etc.; the rodents include mouse, rat, hamster, etc.; and the ungulates include cow, sheep, goat, pig, etc.

Mouse ES cells were first established from the inner cell mass present in the blastocyst which is an early stage embryo of a murine fertilized egg, by Evans, M. J. and Kaufman, M. H. in 1981 (*Nature* 292, 154-156 (1981)). Thereafter, human ES cells were also established from the inner cell mass of human blastcysts by Thomson, J. A. et al. in 1998 (*Science* 282, 1145-1147 (1998)). Similarly, bovine ES-like cells were established from the inner cell mass of bovine blastcysts (JP 2002-153281A).

ES cells are pluripotent stem cells, thus having both an ability to differentiate into any cell, tissue or organ and an ability to proliferate semi-permanently.

ES cells can be prepared from inner masses of mammalian blastcysts by the known methods. For example, this method comprises the steps of: obtaining blastcysts from eggs of a mammal after in vivo or in vitro fertilization; removing the inner cell mass from the blastcysts by micromanipulation; culturing the removed inner cell mass on mouse embryonic fibroblast (MEF) feeders or in feeder-free conditions, in an animal cell culture medium such as Dulbecco's modified eagle medium (DMEM), α-EME medium, Ham's F-12 medium, RPMI1640 medium, or mixtures thereof, for about 1-2 weeks; recovering a ES cells from a culture dish; and subjecting the recovered ES cells to multiple passages by culturing it with or without feeder cells. The culture of the inner cell mass in feeder-free conditions may be carried out on Matrigel or laminin in a medium conditioned by MEF (Xu, C. et al., *Nat. Biothechnol.* 19, 971-974 (2001). The MEF cells may be treated previously with an antibiotic(s) such as mitomycin C, streptomycin, penicillin, etc. The detachment of ES cells from a dish may be carried out by incubating with EDTA or collagenase IV (Laflamme, M. A. et al., *Nat. Biotechnol.* 25, 1015-1024 (2007)). The culture medium can contain substances selected from fetal bovine serum (FBS), basic fibroblast growth factor (bFGF), β-mercaptoethanol (β-ME), non-essential amino acids, glutamate, sodium pyruvate, antibiotics (e.g., penicillin, streptomycin, etc.), and the like, and the culture is generally carried out in an atmosphere of 2-5% $CO_2$ and 98-95% air at about 37-38.5° C. The passage may be carried out at intervals of 3-4 days on MEF feeders or on a plate coated with collagenase I.

The prepared ES cells can generally be identified using their marker genes. Example of the human ES cell marker genes are Oct3/4 (also called Oct3 or Oct4, which is the same protein), alkaline phosphatase, Sox2, Nanog, growth and differentiation factor 3 (GDF3), reduced expression 1 (REX1), fibroblast growth factor 4 (FGF4), embryonic cell-specific gene 1 (ESG1), developmental pluripotency-associated 2 (DPPA2), DPPA4, human telomerase reverse transcriptase (hTERT1), undifferentiated human ES cell-specific surface antigens (SSEA-3, SSEA-4, Tra1-60, Tra1-81), etc. (Takahashi, K. et al., *Cell* 131, 861-872 (2007); Kroon, E. et al., *Nat. Biotechnol.* 26, 443-452 (2008); Xu, C. et al., *Nat. Biotechnol.* 19, 971-974 (2001)). These marker genes are also expressed in the human iPS cell as described in §1.2 below. At least the marker genes for Oct3/4, alkaline phosphatase, Sox2, Nanog, Gdf3, and Fgf4 are expressed in mouse ES cell as well (Takahashi, K. and Yamanaka, S., *Cell* 126, 663-676 (2006)). The presence of the marker genes or gene products can be detected by either RT-PCR or western blotting.

1.2 Preparation of iPS Cells

As described above, the mouse iPS cell was first established by Takahashi, K. and Yamanaka, S. (*Cell* 126, 663-676 (2006); International Publication No. WO2007/069666), then the human iPS cell by Takahashi, K. et al. (*Cell* 131, 861-872 (2007)) and by Yu, J. et al. (*Science* 318, 1917-1920 (2007)) separately.

The iPS cells can be derived from somatic cells by transduction of a somatic cell with the genes encoding at least 3 or 4 or 6 transcription factors, including Oct and Sox family members, as nuclear reprogramming factors. The other transcription factors can be a combination of a Klf family member and optionally a Myc family member, and/or a combination of Nanog and a Lin family member.

Examples of the Oct family members include, but are not limited to, Oct3/4, Oct1A, Oct6, and the like, preferably Oct3/4. Oct3/4 is a transcription factor belonging to the POU (Pit, Oct, Unc) family, and is reported as a marker of undifferentiated cells like embryonic cells, germ cells or ES cells (Niwa, H. *Cell Struc. Func.* 26, 137-148 (2001); Pesce, M. and Scholer, H. R., *Stem Cells* 19, 271-278 (2001)).

Examples of the Sox (SRY-related HMG box) family members include, but are not limited to, Sox1, Sox3, Sox7, Sox15, Sox17, Sox18, and the like, preferably Sox2. Sox2 is a factor which activates the expression of Fgf4 while cooperating with Oct3/4 in pluripotent cells (Yuan, H. et al., *Genes. Dev.* 9, 2635-2645; Avilion, A. A. et al., *Genes Dev.* 17, 126-140 (2003)).

Examples of the Klf (Kruppel like factor) family members include Klf1, Klf2, Klf4, Klf5, and the like, preferably Klf4, which is reported as a tumor repressing factor (Ghaleb et al., *Cell Res.* 15, 92-96 (2005)).

Examples of the Myc family members include c-Myc, N-Myc, L-Myc, and the like, preferably c-Myc, which is a transcription control factor involved in differentiation and proliferation of cells (Adhikary and Eilers, *Nat. Rev. Mol. Cell Biol.* 6, 635-645 (2005)).

Nanog is a homeobox protein, which is expressed the most highly in the inner cell mass of blastcysts but not in differentiated cells (Chambers, L. et al., *Cell* 113, 643-655 (2003); Zaehres, H. et al., *Stem. Cells* 23, 299-305 (2005)).

Examples of the Lin family members include Lin28, which is known as a marker of undifferentiated human ES cell (Richards, M, et al., *Stem Cells* 22, 51-64 (2004)).

More specifically, the combinations of transcription factors are: Oct3/4, Sox2, Klf4 and c-Myc (Takahashi, K. and Yamanaka, S., *Cell* 126, 663-676 (2006); Takahashi, K. et al., *Cell* 131, 861-872 (2007)); Oct3/4, Sox2 and Klf4 (Nakagawa, M. et al., *Nat. Biotechnol.* 26, 101-106 (2008)); and Oct3/4, Sox2, Nanog and Lin28 (Yu, J. et al, *Science* 318, 1917-1920 (2007)). Further, the following combination of six transcription factors can be used: Oct3/4, Nanog, Sox2, Lin28, c-Myc, and Klf4, which can enhance an efficiency of generating iPS cells from human somatic cells (Liao, J. et al., *Cell Res.* 18, 600-603 (2008)). According to Nakagawa, M. et al. (2008), the transduction of human or mouse somatic cells with genes encoding the three transcription factors Oct3/4, Sox2 and Klf4 can drastically inhibit the formation of teratoma, or tumorigenesis.

Genes encoding the nuclear reprogramming factors can separately be prepared from cDNA libraries, which are previously synthesized from mRNA in cells or tissues that each gene is present, by conventional cloning and/or RT-PCR procedures. The sequences of the genes and proteins encoded thereby are available from the GenBank by accessing to the NCBI (USA).

Used as the somatic cells are adult and fetal somatic cells, including primary cells, secondary cells, and cell lines thereof. Examples of somatic cells include any cells from tissues and organs of mammals (preferably, human), including, but not limited to, dermal cells, keratinocytes, liver cells, stomach cells, intestinal cells, spleen cells, renal cells, esophageal cells, bone cells, brain cells, neural cells, glial cells, epitherial cells, epidermal cells, muscle cells, pancreatic cells, and fibroblast cells.

The transduction for generation of iPS cells includes, but is not limited to, uses of vectors, such as viruses and plasmids, lipofection, electropolation, microinjection, and the like. Examples of viral vectors, which are replication-deficient, include, but are not limited to, retrovirus vectors, lentivirus vectors, adenovirus vectors, adeno-associated virus vectors, and the like. Preferably, commercially available vectors may be used as said vectors, and examples of viral vectors are: pMXs, pMYs and pMZs (Cosmo Bio, Japan), which are deficient in gag; retro-XQ vectors (Clontech, the Netherlands), pLenti6/Ubc vectors (Invitrogen, USA), and the like.

In case of the transduction with vectors, genes encoding the nuclear reprogramming factors may be inserted into vector DNAs individually or into a single vector DNA in combination. The genes may be operably linked to a regulatory sequence(s), such as promoter and enhancer, so that they are capable of being expressed. Examples of the promoter are CMV promoter, MSV promoter, RSV promoter, SV40 promoter, and the like. The vectors may further comprise a positive selectable marker(s), such as a drug resistance gene(s) (e.g., puromycin resistance gene, neomycin resistance gene, ampicillin resistance gene, hygromycin resistance gene, or the like), a negative selectable marker(s) (e.g., diphtheria toxin A fragment gene, thymidine kinase gene, or the like), an internal ribosome entry site (IRES), a terminator, an origin of replication, etc.

Somatic cells (for example, $5 \times 10^4$ to $1 \times 10^7$ cells per 100 mm dish) are transduced or transfected with a cocktail of vectors containing the above-described three, four or six nuclear reprogramming factors on MEF feeders or in feeder-free conditions (e.g., on a Matrigel-coated plate) at about 37° C. (Takahashi, K. et al., *Cell* 131, 861-872 (2007)), thereby inducing iPS cells or colonies thereof after about 1-4 weeks of transduction. Culture medium used may be DMEM, α-MEM, Ham's F12 medium, RPMI1640 medium, or mixtures thereof, which medium may contain FBS, antibiotics (e.g., penicillin, streptomycin, etc.), non-essential amino acids, glutamate, sodium pyruvate, β-ME, etc. Then, the generated iPS cells may be maintained in a mouse or primate ES medium supplemented with bFGF. For passage, the iPS cells may be incubated with DMEM/F12 containing collagenase IV (e.g., 1 mg/ml) at about 37° C., and when they are expanded to almost confluent state, the cells are scraped and transferred to a new culture dish on SNL feeder cells. For feeder-free culture of human iPS cells, the cells may be seeded on Matrigel-coated plate in MEF-conditioned or non-conditioned primate ES cell medium, both containing bFGF (e.g., 4 ng/ml), and the medium is exchanged with a fresh medium daily.

Generation of iPS cells can be confirmed by expression of specific marker genes. These marker genes are described in Takahashi, K. and Yamanaka, S. *Cell* 126, 663-676 (2006) for mouse iPS cells, and in Takahashi, K. et al., *Cell* 131, 861-872 (2007) for human iPS cells. These marker genes expressed in human or mouse iPS cells are almost the same as those in human or mouse ES cells, respectively, as described in §1.1 above. The expression of the marker genes for alkaline phosphatase, Oct3/4, Sox2 and Nanog, shows that the generated iPS cells are undifferentiated, ES-like and pluripotent cells. The presence of the marker genes or gene products can be detected by either RT-PCR or western blotting.

For other mammalian iPS cells, one will be able to generate and identify them in similar manners as above.

1.3 Induction and Differentiation of Mesoderm Cells from ES or iPS Cells

According to this invention, when ES or iPS cells, which are differentiating into mesoderm cells, culture in the presence of CSA, the ES or iPS cells differentiate into cardiomyocytes and/or cardiac progenitor cells.

In the invention, the mesoderm cells are characterized in that they are Flk1-positive (i.e., Flk1$^+$), this Flk1$^+$ cells can be induced by culturing ES or iPS cells on collagen IV-coated dishes (LIF(−) and feeder (−)) for 4-5 days by the methods described by Yamashita, J. et al. (*Nature* 408, 92-96 (2000), Yamashita, J. K. et al. (*FASEB J.* 19, 1534-1536 (2005)), or Narazaki, G et al., *Circulation* 118, 498-506 (2008).

Briefly, ES cells are cultured at a cell density of $1-10 \times 10^3$ cells/cm$^2$ in α-MEM as a differentiation medium, containing 10% FCS on collagen IV-coated dishes or mitomycin C-treated confluent OP9 cell sheets (MMC-OP9) for 4.5 days. As for iPS cells, the cells are first plated at a cell density of $1-10 \times 10^3$-$10^4$ cells/cm$^2$ onto gelatin-coated dishes and cultured for 30 min to eliminate attached feeder cells, then non-adhered cells are collected for differentiation. Cells are collected and subjected to fluorescence-activated cell sorting (FACS) to purify Flk1$^+$ cells.

Purified Flk1$^+$ cells are then plated onto MMC-OP9 at a cell density of $1-10 \times 10^3$-$10^4$ cells/cm$^2$ and cultured at about 37° C. for 2-6 days in a differentiation medium (α-MEM supplemented with 10% FCS) containing CSA to induce cardiac differentiation. Medium is replaced every 2 days. Induction of FCV (Flk1$^+$/CXCR4$^+$/vascular endothelial cadherin$^-$) cells and sorting for FCV cells are performed as described (Yamashita, J. K. et al. *FASEB J.* 19, 1534-1536 (2005)). Purified CSA-induced FCV cells have a highly cardiac progenitor activity, which cells express the cardiac progenitor markers such as Flk1, CXCR4, GATA4, Tbx3, Nkx2.5, and islet1 (FIG. 5). The addition of CSA to Flk1+ mesoderm cell cultures results in about 17-fold higher generation of cardiomyocytes and about 22-fold higher generation of FCV progenitors than the cases of non-CSA (FIG. 6).

The concentration of CSA in culture medium is, for example, approximately 0.1-10 µg/mL, preferably approximately 1-3 µg/mL. After 4-6 days of the culture, the ES cell- or iPS cell-derived mesoderm cells are differentiated into self-beating cardiomyocytes, and/or cardiac progenitor cells which have an ability to give rise to cardiomyocytes.

The generation of cardiomyocytes can be confirmed by the following points:

(1) they are beating cells (FIG. 1*a*);
(2) they are positive for cardiac troponin-T (cTnT) (FIGS. 1*b, c*);
(3) they show sarcomere formation (FIG. 1*e*);
(4) action potential in purified cardiomyocytes shows existence of cells with pacemaker potential (FIG. 1*f*); and
(5) ventricular type cells lack pacemaker potential and self-beating (FIG. 1*g*);
(6) purified CSA-induced cardiomyocytes show cardiac marker mRNA expression, such as alpha-myosin heavy chain (MHC), myosin light chain (MLC) 2v and 2a, Nkx2.5, GATA4, and T-box protein 3 (Tbx3) (FIG. 5).

The generation of cardiac progenitor cells can be confirmed by the expression of mRNA for cardiac progenitor markers, such as Flk1, CXCR4, GATA4, Nkx2.5, islet1, but the cardiac progenitor cells do not express the mature cardiomyocyte markers MHC, MLC-2v and MLC-2a (FIG. 5).

According to this invention, in case of ES cells, about 60% of Flk1$^+$ cell-derived cells are changed into cardiomyocytes (FIG. 1h), and the CSA treatment leads to about 17-fold increase in the yield of FACS-purified cardiomyocytes starting from the same number of Flk1$^+$ cells (FIG. 1i). As a result, approximately 200 cardiomyocytes could be obtained from one ES cell (FIG. 6).

Similarly, in case of iPS cells, CSA treatment on purified iPS cell-derived Flk1$^+$ cells markedly increases the appearance of cardiomyocytes by approximately 12 times than the non-treatment with CSA (FIGS. 2a, b), and the CSA treatment also drastically increases FCV cardiac progenitor population. The FCV cells from iPS cell-derived Flk1$^+$ cells increase up to 28% by CSA (FIG. 2c).

Figure 2:
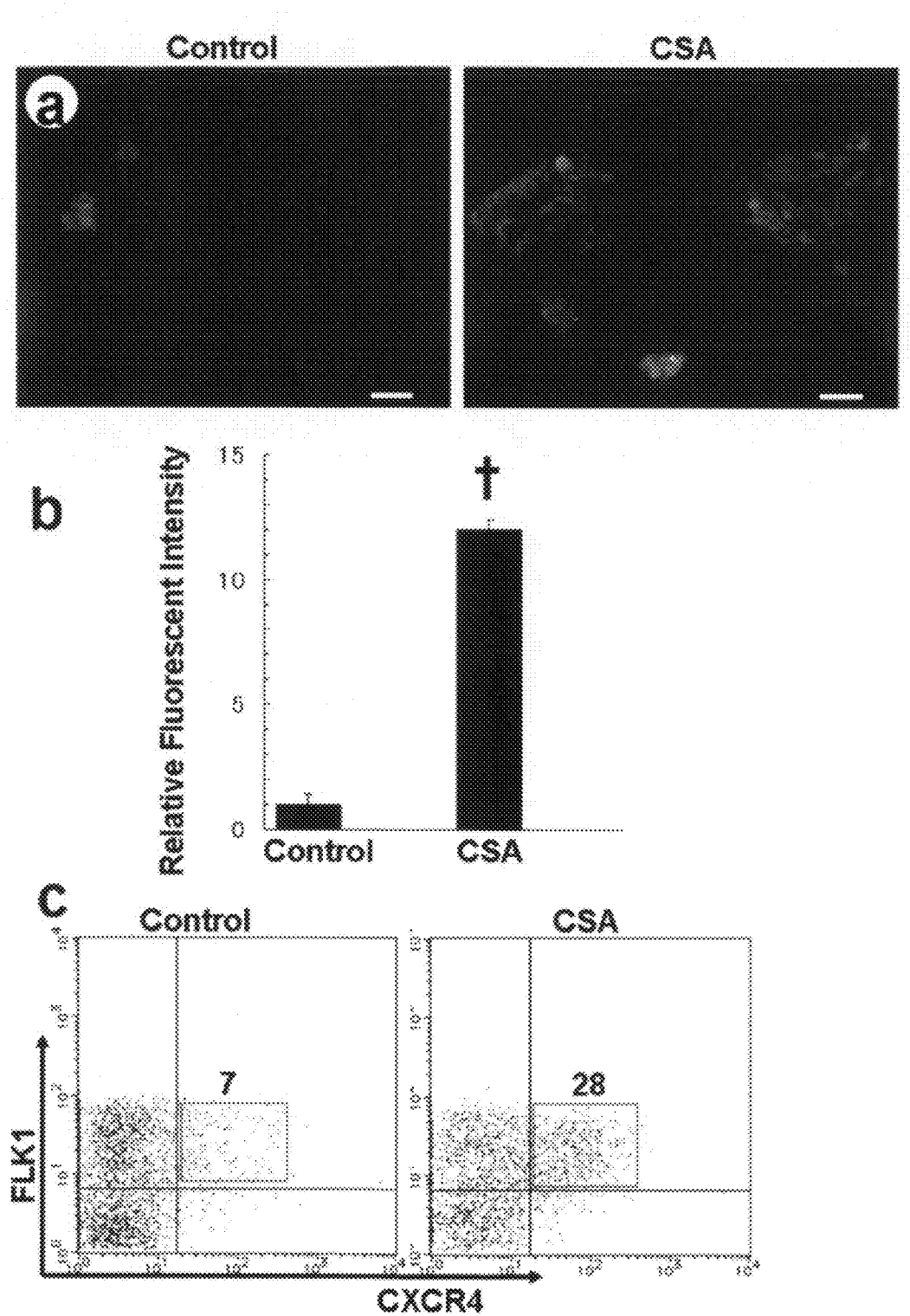
FIG. 2: Induction of cardiomyocytes and cardiac progenitors from iPS cells by CSA treatment.
Figure 2:
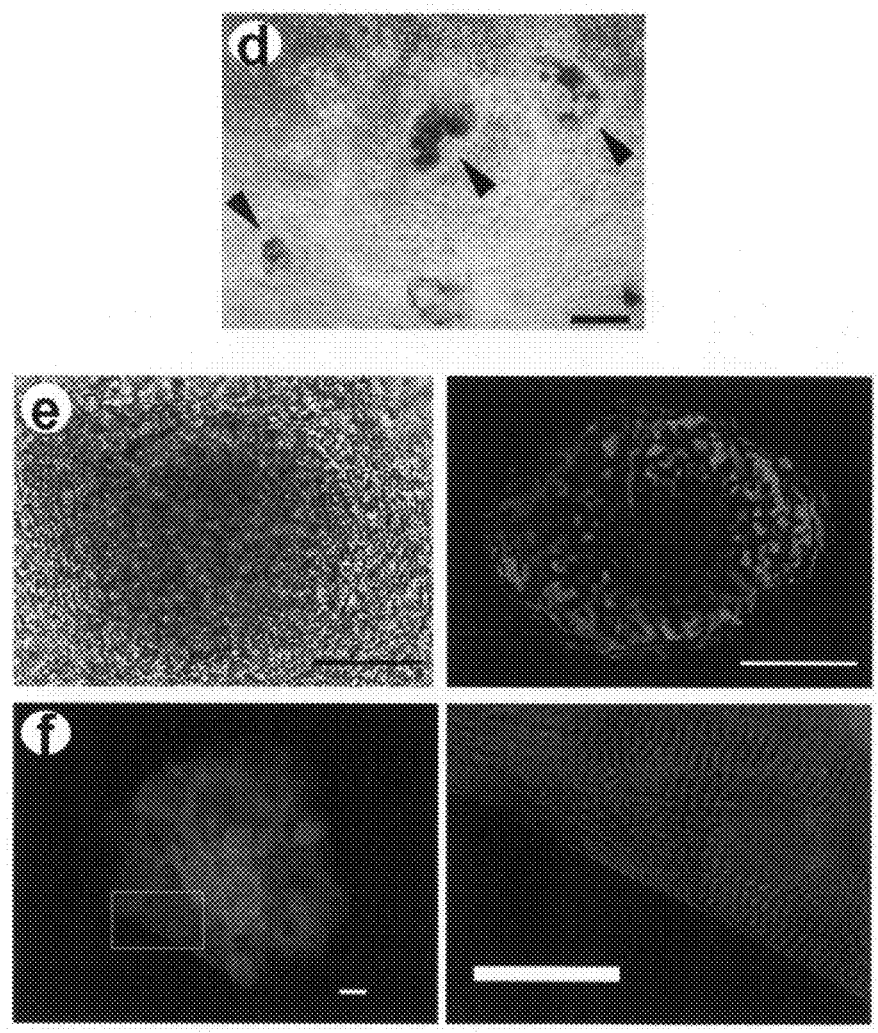
Figure 2:
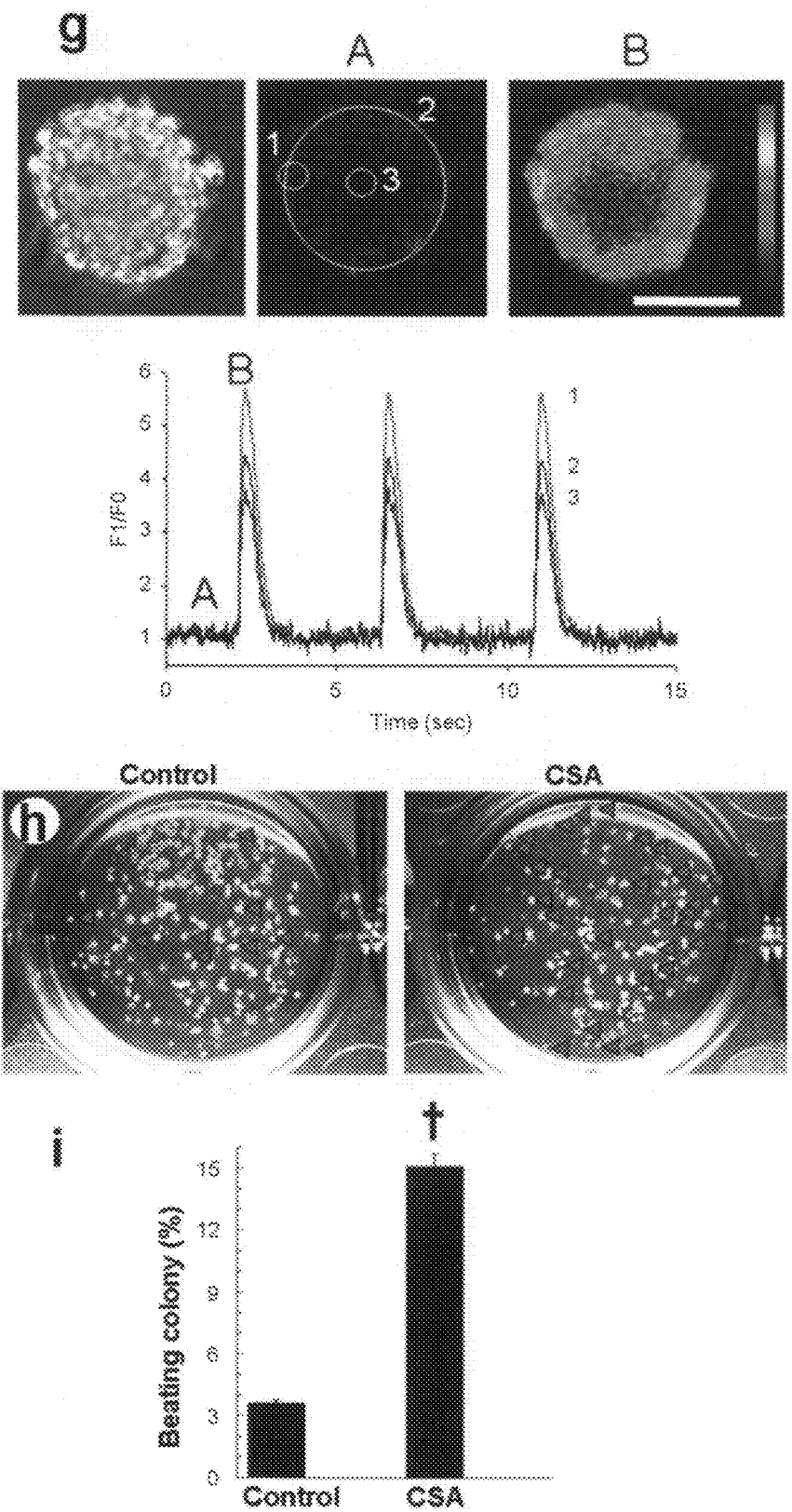

When human iPS cells are cultured on END-2 visceral endodermal stroma cells (Mummery, C. et al. *Circulation* 107, 2733-2740 (2003)), self-beating colonies are observed after approximately 10-12 days of culture (FIG. 2d). The beating cells are positive for cTnT (FIG. 2e), and show apparent sarcomere formation with actinin staining (FIG. 2f). In the beating cells, intracellular Ca$^{2+}$ levels increase in synchronization with contraction (FIG. 2g). These results indicate that functional cardiomyocytes can successfully be induced from human iPS cells by the method of the invention.

Thus, this invention provides a novel method for the efficient generation of cardiac progenitors and cardiomyocytes from ES cells or iPS cells through the newly discovered mesoderm-specific effect of CSA.

Figure 3:
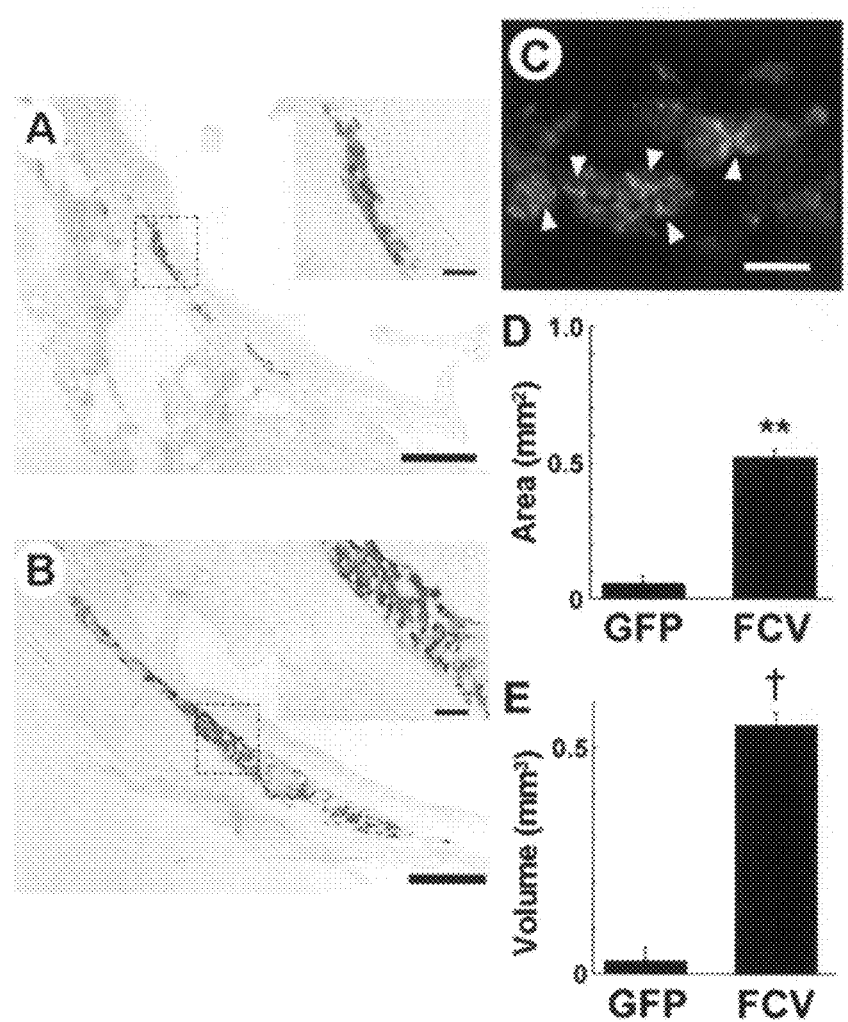
FIG. 3: Efficient contribution of cardiac progenitors to cardiomyocyte regeneration in vivo.

When in vivo differentiation potentials of CSA-expanded FCV cells into cardiomyocytes are examined by transplantation to chronic myocardial infarction model of rat (Tambara, K. et al. *Circulation* 108 suppl II, 259-263 (2003)), the transplanted FCV cells are successfully differentiated into cardiomyocytes and integrated in the infarct heart to form GFP$^+$/cTnT$^+$ donor cell-derived cardiomyocyte layer more effectively in the scar tissue (FIGS. 1l, m; FIG. 3B). Also, the transplanted progenitor cells are successfully differentiated into organized myocardium (FIG. 3C). The transplantation of the FCV cells results in a 8-times higher increase in maximum area of viable regenerated cardiomyocytes than that of the GFP$^+$ cardiomyocyte (FIG. 3D).

The cardiomyocytes, cardiac progenitor cells, or mixtures thereof, which are generated by the method of the invention comprising the use of a combination of FlK1+ mesoderm cells derived from ES or iPS cells and CSA, are also encompassed in the scope of the invention. The CSA-derived cardiomyocytes have an ability to integrate myocardial tissues, and the CSA-derived cardiac progenitor cells are a Flk1+/CXCR4+/vascular endothelial cadherin-cell population, which gives rise to cardiomyocytes. In addition, the CSA-induced cardiomyocytes show the expression of marker mRNAs such as alpha-myosin heavy chain (MHC), myosin light chain (MLC) 2v and 2a, Nkx2.5, GATA4, T-box protein 3 (Tbx3), and the CSA-derived cardiac progenitor cells show the expression of marker mRNAs such as Flk1, CXCR4, GATA4, Nkx2.5, islet1, but not mature cardiomyocytes markers, MHC, MLC-2v, and 2a (FIG. 5).

2. Screening of Agents Capable of Inducing Cardiomyocytes and/or Cardiac Progenitor Cells This invention further provides a method for screening candidate agents for an agent capable of inducing cardiomyocytes and/or cardiac progenitor cells, comprising culturing an iPS cell, which has been differentiated into a mesoderm cell, in the presence of a candidate agent, and selecting said agent based on the formation of beating colonies and/or Flk1$^+$/CXCR4$^+$/vascular endothelial cadherin$^-$ cells.

The culture conditions in the screening system are the same as described in §1.3 above, except that candidate agents are used in place of CSA. Thus, the purified Flk1$^+$ mesoderm cells derived from iPS cells are plated onto MMC-OP9 at a density of 1-10×10$^3$-10$^4$ cells/cm$^2$ and cultured at about 37° C. in a differentiation medium (α-MEM supplemented with 10% FCS) containing a candidate agent, and subsequently it is determined whether cardiac differentiation is induced, by measuring the expression of genes for cardiac progenitor markers and/or cardiomyocyte markers as described in §1.3 above, or by detecting the formation of FCV cardiac progenitor cells or beating colonies. The FCV cardiac progenitor cells are positive for Flk1, positive for CXCR4, and negative for vascular endothelial cadherin (Yamashita, J. K. et al., *FASEB J*. 19, 1534-1536 (2005)), and the presence or absence of these markers is determined by RT-PCR using primers or by FACS or western blotting using antibodies to each marker.

Candidate agents include, but are not limited to, small molecules, peptides, polypeptides, (glyco)proteins, nucleosides, nucleic acids, oligosaccharides, carbohydrates, (glyco) lipids, naturally occurring products, synthetic compounds, inorganic matter, and the like. Hitherto, a combination of activin A and BMP was known as the differentiation inducer (Takahashi, K. et al., *Cell* 131, 861-872 (2007)).

This screening method is characterized by using iPS cell-derived Flk1$^+$ mesoderm cells in the screening system, and by determining the formation of FCV cardiac progenitor cells or beating colonies (cardiomyocytes, cTnT-positive) as an indicator. Agents selected by this method are capable of inducing cardiomyocytes and/or cardiac progenitor cells, thus being usable as novel cardiac regenerative drugs in the regeneration therapy.

3. Therapeutic use of Cardiomyocytes and/or Cardiac Progenitor Cells

This invention further provides a method for treating a subject with heart disease, comprising transplanting the cardiomyocytes, cardiac progenitor cells, or mixtures thereof, which are prepared by procedures as described in §1.3 above, to the heart of the subject.

This invention further provides use of the cardiomyocytes, cardiac progenitor cells, or mixtures thereof, which are prepared by procedures as described in §1.3 above, in manufacture of a medicament or transplant or implant for treating a subject with heart disease.

In the above inventions, cardiac progenitor cells are preferably used.

These inventions provide stem cell-based strategies for cardiac repair or cardiac regeneration. Especially, when the technology of inducing human iPS cells from somatic cells found by the group of Dr. Yamanaka, S (*Cell* 131, 861-872 (2007); *Nat. Biotechnol*. 26, 101-106 (2008)) is fused with the present inventions, it will become possible to effect the stem cell-based strategies for cardiac repair or regeneration not only in females but also in males.

The subject includes mammals as defined above, preferably humans.

The heart disease includes, but is not limited to, heart failure including myocardial infarction and cardiomyopathy.

Recently, Laflamme, M. A. et al. has reported that cardiomyocytes derived from human ES cells using activin A and BMP4 enhanced the function of infracted rat hearts (*Nat. Biotechnol*. 25, 1015-1024 (2007)). We have now also found that the transplantation of cardiac progenitor cells to rat myocardial infarction model results in gross appearance of the transplanted cells at the infarct area and integration of a myocardial tissue, i.e., wall thickening (FIGS. 1*l*, 1*m*, 3B, 3D, 3E). Myocardial infarcts in rats can be induced by 60 min of ischemia then reperfusion (Laflamme, M. A. et al., *ibid*).

According to this invention, the cardiomyocytes, cardiac progenitor cells or mixtures thereof, preferably cardiac progenitor cells, derived from iPS or ES cells are surgically transplanted in a form of implant, transplant or graft, to an infracted region (e.g., infarct region) of the hearts of mammals including human, by means of direct injection. The cell counts of the transplanted cells are $1 \times 10^7$-$1 \times 10^9$ cells for example.

The cell preparations to be transplanted in therapy should be purified and confirmed for their security in in vivo use. The purification of the cells may be carried out by using Percoll gradient and FACS for example. As for security, any risk of tumorigenesis or carcinogenesis should be avoided. Especially, in case of the induction of iPS cells, it may be desirable to avoid use of c-Myc and retroviral vectors. The purified cells are stored in preferably a serum-free medium and should be used within 1-2 days.

The following examples are offered to illustrate this invention and are not to be construed in any way as limiting the scope of this invention.

EXAMPLES

Example 1

Cardiogenic Effect of CSA on ES Cells

In our cardiomyocyte differentiation system, we can identify and purify cell populations at four sequential differentiation stages, that is, undifferentiated ES cells, Flk1$^+$ mesoderm cells, FCV cardiac progenitor cells, and cardiomyocytes (FIG. 4) (Yamashita, J. et al. *Nature* 408, 92-96 (2000); Yamashita, J. K. et al. *FASEB J.* 19, 1534-1536 (2005)). When purified Flk1$^+$ cells are cultured on OP9 stroma cells, self-beating cardiomyocytes appear by 4 days of culture (Flk-d4). When we added CSA to Flk1$^+$ cells to confirm its in vitro effect on cardiomyocyte differentiation before using it in cell transplantation experiments, CSA (1-3 μg/mL) showed a striking effect to increase beating cells at Flk-d6 (experiment 1 in FIG. 4) (FIG. 1*a*). Addition of CSA induced approximately 13 times increase in cardiac troponin-T (cTnT)-positive cardiomyocyte appearance than control (FIG. 1*b, c*). CSA-induced cardiomyocytes showed distinct expression of cTnT (FIG. 1*d*), and sarcomere formation (FIG. 1*e*). Action potential in purified cardiomyocytes showed existence of cells with pacemaker potential (FIG. 1*f*), as well as ventricular type cells lacking pacemaker potential and self-beating (FIG. 1*g*). Purified CSA-induced cardiomyocytes showed various cardiac marker mRNA expression, such as alpha-myosin heavy chain (MHC), myosin light chain (MLC) 2v and 2a, Nkx2.5, GATA4, T-box protein 3 (Tbx3) (FIG. 5). These results indicate that functional cardiomyocytes were successfully induced and expanded by CSA treatment. At optimal conditions, approximately 60% of Flk1$^+$ cell-derived cells became cardiomyocytes, positive for MHC promoter-driven GFP (GFP$^+$) (Yamashita, J. K. et al. *FASEB J.* 19, 1534-1536 (2005)) (FIG. 1*h*). The CSA treatment resulted in approximately 17-fold increase in the yield of FACS-purified cardiomyocytes starting from the same number of Flk1$^+$ cells (FIG. 1*i*). As a result, approximately 200 cardiomyocytes could be obtained from one ES cell (FIG. 6).

We further evaluated differentiation stage-specific effects of CSA. CSA did not influence on Flk1$^+$ mesoderm cell appearance from undifferentiated ES cells or endoderm and ectoderm marker expression in early differentiation process (experiment 2 in FIG. 4) (FIG. 7). Surprisingly, addition of CSA to Flk1$^+$ cells specifically increased FCV (Flk1$^+$/CXCR4$^+$/vascular endothelial cadherin$^-$) cardiac progenitor population (Yamashita, J. K. et al. *FASEB J.* 19, 1534-1536 (2005)) to approximately 10-20 times more than control (experiment 3 in FIG. 4). The maximum percentage of FCV cells within total Flk1$^+$ cell-derived cells was increased up to 40% by CSA (FIG. 1*j*). The yield of purified FCV progenitor cells was increased approximately 22 times by CSA treatment (FIG. 1*k*). Purified CSA-induced FCV cells showed various cardiac progenitor marker mRNA expression, such as Flk1, CXCR4, GATA4, Nkx2.5, islet1, but not mature cardiomyocytes markers, MHC, MLC-2v, and 2a (FIG. 5). Single FCV cells could give rise to cardiomyocytes as well as ECs and MCs on OP9 cells (FIG. 8). Comparable number of cardiomyocytes was induced on OP9 cells from the same number of control FCV cells and CSA-expanded FCV cells. In vivo differentiation potentials of CSA-expanded FCV cells to cardiomyocytes were examined by transplantation to chronic myocardial infarction model of rat (Tambara, K. et al. *Circulation* 108 suppl II, 259-263 (2003)). Transplanted FCV cells were successfully differentiated into cardiomyocytes and integrated in the infarct heart to form GFP$^+$/cTnT$^+$ donor cell-derived cardiomyocyte layer more effectively in the scar tissue (FIGS. 1*l, m*; FIG. 3B), when compared with the case where GFP$^+$ cardiomyocytes were transplanted (FIG. 3A). Connexin43 was observed among adjacent cTnT$^+$ cells, suggesting that transplanted progenitor cells successfully differentiated into organized myocardium (FIG. 3C). FCV cell transplantation showed more than 8 times increase in maximum area of viable regenerated cardiomyocytes than that induced by GFP$^+$ cardiomyocyte transplantation (FIG. 3D). Estimated volumes of regenerated myocardium increased approximately 23 times more by FCV cell injection than that of GFP$^+$ cells (FIG. 3E). These results indicate that CSA-expanded FCV cells possess highly cardiogenic potentials both in vitro and in vivo. EdU incorporation and annexin V expression in FCV cells and cardiomyocytes were not affected by CSA treatment (FIGS. 9, 10), indicating that the increase in FCV cells and cardiomyocytes by CSA was not due to proliferation and/or survival of FCV cells and cardiomyocytes. When CSA was added to purified FCV cells, (experiment 4 in FIG. 4) slight increase (approximately 2.6-times) in cardiomyocytes was observed (FIG. 1*l*).

We further examined cellular and molecular mechanisms of CSA. CSA treatment on Flk1$^+$ cells (Flk-d0-6: experiment 1 in FIG. 4) induced drastic increase in cardiomyocytes with reciprocal decrease in ECs or blood cells from Flk1$^+$ cells (FIG. 1*n*, FIG. 12). Even when CSA was added only during mesoderm stage (Flk-d0-2: experiment 5), similar effects were observed (FIG. 13), suggesting that CSA should act on Flk1$^+$ cells and may shift the cell fate from ECs or blood cells to cardiomyocytes. Calcineurin inhibitors, CSA and FK506 exert their immunosuppressing effect through inhibition of nuclear factor of activated T-cells (NF-AT) signaling (Martinez, S. & Redondo, J. M. *Curr Med Chem.* 11, 997-1007 (2004)). Nevertheless, FK506 and a NF-AT inhibitor, 11R-VIVIT, showed no significant effect on cardiomyocyte induction in our system (FIG. 14), suggesting that the main cardiogenic effect of CSA should be NF-AT independent. Mesoderm-specific addition of wnt3a and TGF-β to Flk1$^+$ cells (Flk-d0-2: experiment 5 in FIG. 4) showed significant decrease in cardiomyocytes at Flk-d6 (FIG. 15). On the contrary, mesoderm-specific addition of Dkk1 significantly increased in cardiomyocytes at Flk-d6 (FIG. 15). The effect of Dkk1 was, however, much weaker than that of CSA. These results indicate that the potent cardiomyocyte inducing activity of CSA should be evoked through novel mechanisms to induce specific and efficient expansion of the cardiac progenitor cells in mesoderm-specific, NF-AT independent fashion.

Example 2

Cardiogenic Effect of CSA on iPS Cells

We further examined the cardiogenic effect of CSA on iPS cells. Recently, we demonstrated that mouse iPS cells (Okita, K. et al., Nature 448, 313-317 (2007)) could give rise to cardiomyocytes using the identical differentiation method for mouse ES cells (Yamashita, J. K. et al. FASEB J. 19, 1534-1536 (2005); Narazaki, G, et al. Circulation 118, 498-506 (2008)). CSA treatment on purified iPS cell-derived Flk1$^+$ cells markedly increased the cardiomyocyte appearance by approximately 12 times than control (FIGS. 2a, b). CSA treatment also drastically increased FCV cardiac progenitor population in iPS cells. The maximum percentage of FCV cells from iPS cell-derived Flk1$^+$ cells was increased up to 28% by CSA. (FIG. 2c).

Next, we examined cardiomyocyte differentiation from human iPS cells (Nakagawa, M. et al. Nat. Biotechnol. 26, 101-106 (2008)). When human iPS cells were cultured on END-2 visceral endodermal stroma cells (Mummery, C. et al. Circulation 107, 2733-2740 (2003)), self-beating colonies were observed after approximately 10-12 days of culture (FIG. 2d). Beating cells were positive for cTnT (FIG. 2e), and showed apparent sarcomere formation with actinin staining (FIG. 2f). Fluo-8 imaging revealed that intracellular Ca$^{2+}$ increases in synchronization with contraction (FIG. 2g). These results indicate that functional cardiomyocytes were successfully induced from human iPS cells by this method.

Finally, we examined the mesodermal effect of CSA on the cardiomyocyte induction from human iPS cells. Recently, we demonstrated that VEGFR2$^+$ mesoderm cells appeared from human ES cells approximately 8 days after the differentiation (Sone, M. et al. Arterioscler. Thromb. Vasc. Biol. 27, 2127-2134 (2007)). mRNA expression patterns during human iPS cell culture on END2 cells also revealed differentiation kinetics of human iPS cells to cardiomyocytes (FIG. 16), suggesting that the mesoderm induction in human iPS cells should occur around 6-8 days of the differentiation. Addition of CSA to differentiating human iPS cells at the mesoderm stage (i.e. at day 8 of differentiation), but not at undifferentiated stage (day 0 of differentiation), drastically increased appearance of beating colonies (FIG. 2h). Although the number of total colonies that appeared was not different, percentage of beating colonies within the total colonies that appeared increased approximately 4.2 times by CSA-treatment (FIG. 2i), suggesting that CSA should shift the fate of differentiating human iPS cells towards cardiomyocytes at the mesoderm stage. Though cardiac progenitor cells in human iPS cells have not been identified yet, the mesoderm stage-specific effect of CSA strongly suggests the cardiac progenitor expansion by CSA in human iPS cells. CSA treatment, thus, similarly enhanced cardiomyocyte induction from iPS cells through mesoderm-specific fashion.

Thus, this invention provides a novel technology for the specific and efficient expansion of highly cardiogenic progenitors as well as cardiomyocytes from ES cells or iPS cells with a newly discovered mesoderm-specific effect of CSA. Recently, a weak inductive effect of CSA on cardiomyocytes in embryoid bodies was reported (Sachinidis, A. et al. Cell. Physiol. Biochem. 18, 303-314 (2006)). Our novel sequential cardiomyocyte differentiation system should succeed in distinctively digging out the potent mesoderm-specific effect of CSA, which has been buried in the cell mixture of embryoid bodies. This novel culture system would be amenable to screen and discover novel cardiac regenerative drugs from small molecules using chemical biology strategies.

FCV cells, which are detected at 6-6.5 days after the differentiation of mouse ES cells and at 1-2 days before cardiomyocyte appearance, are, to our knowledge, the first identified distinct cardiac progenitor population (Yamashita, J. K. et al. FASEB J. 19, 1534-1536 (2005)) and so far the nearest upstream cardiac progenitors to cardiomyocytes. Recently, several kinds of multipotent cardiac progenitor populations were reported (Kattman, S. J. et al, Dev. Cell 11, 723-32 (2006); Wu, S. M. et al. Cell 127, 1137-1150 (2006); Moretti, A. et al. Cell 127, 1151-1165 (2006)). Cardiac progenitors reported by Kattman et al were identified at earlier stage of differentiation (i.e. at 4.25 days after the differentiation) than FCV cells[21]. Other Nkx2.5$^+$ or islet1$^+$ cardiac progenitors were reported at 4-6 days of ES cell differentiation (Wu, S. M. et al. Cell 127, 1137-1150 (2006); Moretti, A. et al. Cell 127, 1151-1165 (2006)). In our FCV population, approximately 42% of cells were Islet1$^+$, 24% were Nkx2.5$^+$, and 14% were double positive for Islet1 and Nkx2.5 (FIG. 17). Moreover, FCV cells also share the differentiation potentials to ECs and MCs (FIG. 8), similar to Islet1$^+$/Nkx2.5$^+$ progenitors. FCV cells, thus, should be an overlapped population with Nkx2.5$^+$ and/or Islet1$^+$ cardiac progenitors.

To our knowledge, this is the first report for specific expansion of cardiac progenitors and cardiomyocytes from iPS cells. Our efficient method of cardiomyocyte induction from iPS cells would be a critical technological basis to generate patient-specific cellular models of cardiomyocytes (Yamanaka, S. Cell Stem Cell 1, 39-49 (2007)). Recently, a cardiac mesoderm/progenitor population was identified using human ES cells (Yang, L. et al. Nature 453, 524-528 (2008)). Identification, efficient induction, and purification of cardiac progenitors from human iPS cells would be certainly important for cell-based cardiac regeneration. This novel cardiac differentiation technology, thus, would broadly contribute to develop cardiac regenerative medicine by providing various options for cell sources, transplantation strategies, and drug discovery.

Experimental Procedures for Examples 1 and 2

Antibodies

Monoclonal antibodies (MoAbs) for murine E-cadhein (ECCD2), murine Flk1 (AVAS12) were prepared and labeled in our laboratory as described previously (Yamashita, J. et al. Nature 408, 92-96 (2000); Yamashita, J. K. et al. FASEB J. 19, 1534-1536 (2005)). MoAb for cardiac troponin-T (cTnT) (1:2000) was purchased from NeoMarkers (Fremont, Calif.). For staining human iPS cells, MoAbs for cTnT (1:100) was from Santa Cruz Biotechnology (Santa Cruz, Calif.). MoAbs for murine α-actinin (1:800) was from Sigma (St Louis, Mo.). MoAb of PE-conjugated AVAS12 was purchased from eBioscience (San Diego, Calif.). MoAbs for mouse CD31 (for immunostaining, 1:200) and Biotinylated-CXCR4 was purchased from BD Pharmingen (San Diego, Calif.). Polyclonal rabbit antibody to GFP (1:500) was purchased from MBL (Nagoya, Japan).

Reagents

Cyclosporin-A (a gift from Novartis Pharma) was dissolved in Dimethyl sulfoxide (DMSO) (Nacalai Tesque, Kyoto Japan) at 30 mg/mL. Dilution of 1-3 µg/mL was made in differentiation medium at the time of use. FK506 (a gift from Astellas Pharma Inc) was dissolved in DMSO at 10 mg/mL, dilution of 10 ng-1 ug/mL was made in differentiation medium. 11R-VIVIT was from Calbiochem (Darmstadt, Germany). Wnt3a, Dkk-1 and TGF-β were from R&D Systems (Minneapolis, Minn.). Annexin V-FITC or PE was purchased from BD pharmingen (San Diego, Calif.). Click-iT™ EdU Alexa Fluor488 Imaging Kit was from Invitrogen (Carlsbad, Calif.). PKH67 fluorescent dye was purchased from Sigma (St. Louis, Mo.).

Mouse ES and iPS Cell Culture

EMG7 mouse ES cells that carry mouse α-myosin heavy chain (MHC) promoter-driven EGFP gene were used for this study (Yamashita, J. K. et al. *FASEB J.* 19, 1534-1536 (2005)). Germline-competent mouse iPS cell lines, 20D-17, 38C-2, and 38D-2, carrying Nanog promoter-driven GFP/IRES/puromycin resistant gene (Nanog-iPS cells), were maintained as previously described[2]. Briefly, iPS cells were maintained in Dulbecco's Modified Eagle Medium (DMEM) containing 15% FCS, non-essential amino acids, 1 mmol/L sodium pyruvate, 5.5 mmol/L 2-mercaptoethanol, 50 units/mL penicillin and 50 mg/mL streptomycin on feeder layers of mitomycin-C-treated mouse embryonic fibroblast (MEF) cells carrying stably incorporated puromycin-resistance gene. OP9 stroma cells were maintained as described (Nishikawa, S. I. et al. *Development* 125, 1747-1757 (1998)).

Human ES and iPS Cell Culture

END-2 cells (a gift from Dr. Mummery) were cultured as described previously (Mummery, C. et al. *Circulation* 107, 2733-2740 (2003)). Myc-negative human iPS cell lines, 253G1 and 253G4 were maintained as previously described (Nakagawa, M. et al. *Nat. Biotechnol.* 26, 101-106 (2008)). Induction of cardiomyocyte differentiation from human iPS cells was performed by co-culturing clots of undifferentiated human iPS cells on END-2 cells, being based on the method previously described (Mummery, C. et al. *Circulation* 107, 2733-2740 (2003); Passier, R. et al. *Stem Cells* 23, 772-780 (2005)). To study the effect of CSA on cardiomyocyte differentiation, 2 µg/mL CSA was added to the culture medium on day 0 or 8 after start of co-culture. The beating colony number on day 12 was scored by microscopic examination. For intracellular $Ca^{++}$ measurement and immunostaining of actinin, beating colonies were mechanically excised, gently dissociated by trypsin-EDTA treatment, and replated onto gelatin-coated dishes.

As an example, human iPS cells can be generated from adult human dermal fibroblasts (HDF) as follows.

We introduced with pMXs (retroviral vectors) encoding human Oct3/4, Sox2 and Klf4 (and ±c-Myc) into HDF-Slc7a1 ($8\times10^5$ cells per 100 mm dish). The human Oct3/4, Sox2, Klf4, and Myc was separately cloned from a human tissue library by RT-PCR using the following sense ("S") and antisense ("AS") primers:

```
                                        (SEQ ID NO: 1)
hOCT3/4-S, CACCATGGCGGGACACCTGGCTTCAG;

(SEQ ID NO: 2)
hOCT3/4-AS, ACCTCAGTTTGAATGCATGGGAGAGC;

(SEQ ID NO: 3)
hSOX2-S, CACCATGTACAACATGATGGAGACGGAGCTG;

(SEQ ID NO: 4)
hSOX2-AS, TCACATGTGTGAGAGGGGCAGTGTGC;
```

-continued
```
                                        (SEQ ID NO: 5)
hKLF4-S, CACCATGGCTGTCAGTGACGCGCTGCTCCC;

(SEQ ID NO: 6)
hKLF4-AS, TTAAAAATGTCTCTTCATGTGTAAGGCGAG;

(SEQ ID NO: 7)
hMYC-S, CACCATGCCCCTCAACGTTAGCTTCACCAA;

(SEQ ID NO: 8)
hMYC-AS, TCACGCACAAGAGTTCCGTAGCTGTTCAAG.
```

Six days after transduction, the cells were harvested by trypsinization and plated onto mitomycin C-treated SNL feeder cells (McMahon and Bradley, Cell 62, 1073-1085 (1990)) at $5\times10^4$ or $5\times10^5$ cells per 100-mm dish. The next day, the medium (DMEM containing 10% FBS) was replaced with a medium for primate ES cell culture supplemented 4 ng/ml basic fibroblast growth factor (bFGF). Approximately 2 weeks later, some granulated colonies were appeared, which colonies were not similar to hES cells in morphology. Around day 25, we observed distinct types of colonies that were flat and resembled hES cell colonies. From $5\times10^4$ fibroblasts, we observed ~10 hES cell-like colonies and ~100 granulated colonies. At day 30, we picked hES cell-like colonies and mechanically disaggregated them into small clumps without enzymatic digestion. When starting with $5\times10^5$ fibroblasts, the dish was nearly covered with more than 300 granulated colonies. We occasionally observed some hES cell-like colonies in between the granulated cells.

The hES-like cells expanded on SNL feeder cells under the human ES cell culture conditions. They formed tightly packed and flat colonies. Each cell exhibited morphology similar to that of human ES cells, characterized by large nucleoli and scant cytoplasm. As is the case with hES cells, we occasionally observed spontaneous differentiation in the center of the colony.

These cells also showed similarity to hES cells in feeder dependency. They did not attach to gelatin-coated tissue-culture plates. By contrast, they maintained an undifferentiated state on Matrigel-coated plates in MEF-conditioned medium (MEF-CM), but not in ES medium.

The cells selected after transduction of HDF were human iPS cells, whose properties including morphology were as described by Nakagawa et al. (*Nat. Biotechnol.* 26, 101-106 (2008)).

Induction of Cardiomyocyte Differentiation

Induction of Flk1+ cells and sorting for Flk1+ cells were performed as previously described (Yamashita, J. et al. *Nature* 408, 92-96 (2000); Yamashita, J. K. et al. *FASEB J.* 19, 1534-1536 (2005)). Briefly, mouse ES cells (or iPS cells) were cultured at cell density $1\text{-}2.5\times10^3$ cells/cm² in differentiation medium (alpha minimum essential medium (GIBCO, Grand Island, N.Y.) supplemented with 10% fetal calf serum) on type IV collagen-coated dishes (Biocoat, Beckton Dickinson) or mitomycin C-treated confluent OP9 cell sheets (MMC-OP9) for 96-108 h. (As for iPS cells, cells were first plated onto gelatin-coated dishes and cultured for 30 min to eliminate attached feeder cells, then, non-adhered cells were collected and subjected to differentiation.) Cells were collected and subjected to FACS to purify Flk1+ cells. Purified Flk1+ cells were then plated onto MMC-OP9 at cell density of $1\text{-}10\times10^3$ cells/cm² and cultured in differentiation medium to induce cardiac differentiation. Medium was replaced every 2 days. Induction of FCV cells and sorting for FCV cells were performed as described (Yamashita, J. K. et al. *FASEB J.* 19, 1534-1536 (2005)). Purified FCV progenitor cells were again plated onto MMC-OP9 cells. MMC-OP9 cells were prestained with PKH67 fluorescent dyes (Sigma) before plating. CSA (1-3 μg/mL) was added to undifferentiated ES cells, Flk1+ cells, or FCV cells on OP9 cells. CSA was added repetitively together with medium replacement in every 2 days. The same dilutions of DMSO alone were used as control.

Flowcytometry and Cell Sorting

FACS for differentiating ES cells (or iPS cells) was performed as described previously (Yamashita, J. et al. *Nature* 408, 92-96 (2000); Yamashita, J. K. et al. *FASEB J.* 19, 1534-1536 (2005)). After 96-108 h of ES cell differentiation, cultured cells were harvested and stained with allophycocyanin (APC)-conjugated AVAS12 and FITC-conjugated ECCD2. Viable Flk1+/E-cadherin− cells, excluding propidium iodide (Sigma), were sorted by FACS Vantage (Becton Dickinson). For FACS for FCV progenitor cells, after 2 days differentiation of purified Flk1+ cell on PKH67-stained OP9 cells (Flk-d2), cultured cells were harvested and stained with a combination of MoAbs of PE-conjugated AVAS12 and biotinylated CXCR4 followed by addition of streptoavidin-conjugated APC, and subjected to FACS analysis. PKH-negative populations were analyzed and sorted as ES cell-derived cells. Flk1+/CXCR4+ population (which was vascular endothelial cadherin-negative (Yamashita, J. K. et al. *FASEB J.* 19, 1534-1536 (2005))), was evaluated and sorted as FCV cardiac progenitor cells. For FACS for cardiomyocytes, cells were harvested after 6 days culture of Flk1+ cells on OP9 cells (Flk-d6), GFP+ population was evaluated and sorted as differentiated cardiomyocytes.

Immunohistochemistry

Immunostaining for ECs and cardiomyocytes were performed as described (Yamashita, J. K. et al. *FASEB J.* 19, 1534-1536 (2005)). Briefly, 4% paraformaldehyde (PFA)-fixed cells were blocked by 2% skim milk (BD, bioscience) and incubated with 1$^{st}$ Abs. For immunohistochemistry, anti-mouse IgG-conjugated with horse radish peroxidase (HRP) (Invitrogen) was used as 2$^{nd}$ Abs. For immunofluorescent staining, anti-mouse, rat and Rabbit Ig-conjugated with Alexa 488 or 546 were used for 2$^{nd}$ Abs. Nuclei were visualized with DAPI (Invitrogen). The hearts were perfused retrogradely from apex of left ventricle, fixed with 4% buffered paraformaldehyde for 2 hours at 4° C., embedded with O.C.T compound (Tissue-Tek; Miles, Inc.), and transversely sectioned in 6 μm thickness. Double staining for cTnT and GFP was performed with mixture of first Abs, anti-cTnT labeled with Zenon Alexa Fluor 546 labeling kit (molecular Probes) and anti-GFP, followed by secondary antibody, Alexa Fluor488-conjugated anti-Rabbit Ig (1:500) (Molecular Probes). Stained cells were photographed with inverted fluorescent microscopy, Eclipse TE2000-U (Nikon, Tokyo, Japan), digital camera system, AxioCam HRc (Carl Zeiss, Germany), or BIOREVO BZ-9000 (Keyence Osaka, Japan).

Quantification of Cardiomyocyte Differentiation

Cardiomyocyte differentiation was quantitatively evaluated by fluorescent intensity of cTnT staining using Alexa Fluor 546 as described (Yamashita, J. K. et al., *FASEB J.* 19, 1534-1536 (2005). Images of stained cells were captured with digital CCD camera, Cool SNAP-HQ (Roper, Atlanta, Calif.), and calculated with an image informatics software, Image-Pro Plus (Media Cybernetics, Silver Spring, Md.). Nineteen vision fields of ×40 magnification in every well of a 24-well plate were automatically selected with motorized X-Y stage, ProScan Stages (Planetron, Tokyo, Japan), equipped on inverted fluorescent microscopy controlled by Stage-Pro module of Image-Pro Plus (Media Cybernetics). Summation of total fluorescent intensity from 19 vision fields was defined as amount of cardiomyocytes that appeared.

Model of Heart Failure

All experimental procedures were performed in accordance with the guidelines for Animal Experiments of Kyoto University, which conforms to the law of "Guide for the Care and Use of Labotatory Animals" in Japan. We used male F344/nru nude rats (Kyoto University, Japan) weighing 235-255 g. Myocardial infarction was created by proximal ligation of the left coronary artery through left thoracotomy, as described previously (Tambara, K. et al. *Circulation* 108 suppl II, 259-263 (2003)).

ES Cell Transplantation.

Four weeks after ligation, 6 rats with moderate-sized myocardial infarction (MI) (infarct size: 20-40%) were used for cell transplantation experiment. Through left thoracotomy, after putting mattress sultures with 6.0 polypropylene thread at injection points to prevent leakage, 100 μL culture medium containing $4 \times 10^5$ cells were subepicardially injected into the center of the scar using a 27-gauge needle. Bulging over the MI area was confirmed after injection. Anesthetic or surgical procedures are described (Tambara, K. et al. *Circulation* 108 suppl II, 259-263 (2003)).

Electrophysiological Studies

FACS-purified GFP positive cardiomyocytes population was seeded on gelatin-coated coverslips. The cells were cultured for 2-4 days and the coverslips were then transferred to a patch clamp recording chamber. The cells showing GFP-fluorescence (excitation at 480±20 nm and emission 535±25 nm) were used for the membrane potential measurement with a patch clamp amplifier (Axopatch200B, Axon Instruments/Molecular Devices Corp., Union City, Calif.). All experiments were performed at 36-37° C.

Composition of Solutions: Bath solution contained (in mmol/L) 140 NaCl 5.4 KCl, 0.33 NaH2PO4, 0.45 MgCl2, 1.8 CaCl2, and 5 HEPES (pH=7.4 with NaOH). Pipette solution contained (in mmol/L) 110 L-Aspartic acid, 30 KCl, 5 MgATP, 0.1 NaGTP, 5 K2Creatine phosphate, 2 EGTA, 10 HEPES, and 10 NaOH (pH=7.2 with KOH).

Intracellular $Ca^{2+}$ Measurement

Human iPS cells were loaded with 1 μM Quest Fluo-8 (ABD Bioquest, Inc. Sunnyvale, Calif.) for 30 min. Fluo-8 fluorescence (excitation at 495±10 nm and emission at 535±20 nm) of beating colony was measured every 16 msec with a back-thinned electron multiplier CCD camera (ImagEM Hamamatsu Photonics K. K. Hamamatsu, Japan). Three consecutive images were averaged. The change of the fluorescence intensity of the iPS colony, from which background fluorescence was subtracted, was expressed as ratio (F1/F0) of the intensity to the one at the beginning of recording (F0). The measurement was carried out at room temperature.

Reverse-Transcription Polymerase Chain Reation (RT-PCR)

Total RNA was isolated from various kinds of cell populations by using RNeasy Mini Kit (QIAGEN, Valencia, Calif.). cDNA was synthesized by SuperScript III First-strand Synthesis System (Invitrogen). PCR reaction was performed using KOD plus (Toyobo, Tokyo, Japan). Primers that were used are indicated in Table I and Table II.

TABLE I

Primer list for RT-PCR (mouse ES cells)

| Gene | | Sequence | |
|---|---|---|---|
| CXCR4 | Forward | TAGGATCTTCCTGCCCACCAT | (SEQ ID NO: 9) |
| | Reverse | TGACCAGGATCACCAATCCA | (SEQ ID NO: 10) |
| Flk1 | Forward | GGCGGTGGTGACAGTATCTT | (SEQ ID NO: 11) |
| | Reverse | CTCGGTGATGTACACGATGC | (SEQ ID NO: 12) |
| GATA4 | Forward | TCTCACTATGGGCACAGCAG | (SEQ ID NO: 13) |
| | Reverse | GCGATGTCTGAGTGACAGGA | (SEQ ID NO: 14) |
| Tbx3 | Forward | CAACAACATATCGGATAAACAGG | (SEQ ID NO: 15) |
| | Reverse | AAAGTACTGTAAGGCAGTTTCAGGAT | (SEQ ID NO: 16) |
| Nkx2.5 | Forward | CAAGTGCTCTCCTGCTTTCC | (SEQ ID NO: 17) |
| | Reverse | GGCTTTGTCCAGCTCCACT | (SEQ ID NO: 18) |
| Islet1 | Forward | ATGATGGTGGTTTACAGGCTAAC | (SEQ ID NO: 19) |
| | Reverse | TCGATGCACTTCACTGCCAG | (SEQ ID NO: 20) |
| Alpha-MHC | Forward | GAGATTTCTCCAACCCAG | (SEQ ID NO: 21) |
| | Reverse | TCTGACTTTCGGAGGTACT | (SEQ ID NO: 22) |
| MLC-2v | Forward | AAAGAGGCTCCAGGTCCAAT | (SEQ ID NO: 23) |
| | Reverse | CCTCTCTGCTTGTGTGGTCA | (SEQ ID NO: 24) |
| MLC-2a | Forward | TCAGCTGCATTGACCAGAAC | (SEQ ID NO: 25) |
| | Reverse | AAGACGGTGAAGTTGATGGG | (SEQ ID NO: 26) |
| Brachyury | Forward | CTCCAACCTATGCGGACAAT | (SEQ ID NO: 27) |
| | Reverse | CCCCTTCATACATCGGAGAA | (SEQ ID NO: 28) |
| AFP | Forward | TGAAGAGGGAAGACATAACTG | (SEQ ID NO: 29) |
| | Reverse | AGCAGCCCAAAGAAGAAT | (SEQ ID NO: 30) |
| Foxa2 | Forward | CCCATTCCAGCGCTTCTC | (SEQ ID NO: 31) |
| | Reverse | GTAATGGTGCTCGGGCTTC | (SEQ ID NO: 32) |
| Nestin | Forward | GAGGAAGAAGATGCTGATGAAGA | (SEQ ID NO: 33) |
| | Reverse | GCCACTGATATCAAAGGTGTCTC | (SEQ ID NO: 34) |
| Pax6 | Forward | CGGAGAAGACTCGGATGAAG | (SEQ ID NO: 35) |
| | Reverse | GGCCCTTCGATTAGAAAACC | (SEQ ID NO: 36) |
| β-actin | Forward | GCTCGTCGTCGACAAGGGCTC | (SEQ ID NO: 37) |
| | Reverse | CAAACATGATCTGGGTCATCTTCTC | (SEQ ID NO: 38) |

TABLE II

Primer list for RT-PCR (human iPS cells)

| Gene | | Sequence | |
|---|---|---|---|
| Oct3/4 | Forward | AACCTGGAGTTTGTGCCAGGGTTT | (SEQ ID NO: 39) |
| | Reverse | TGAACTTCACCTTCCCTCCAACCA | (SEQ ID NO: 40) |
| Brachyury-T | Forward | CAGTGGCAGTCTCAGGTTAAGAAGGA | (SEQ ID NO: 41) |
| | Reverse | CGCTACTGCAGGTGTGAGCAA | (SEQ ID NO: 42) |
| KDR | Forward | ACTTTGGAAGACAGAACCAAATTATCTC | (SEQ ID NO: 43) |
| | Reverse | TGGGCACCATTCCACCA | (SEQ ID NO: 44) |
| islet1 | Forward | TTGTACGGGATCAAATGCGCCAAG | (SEQ ID NO: 45) |
| | Reverse | AGGCCACACAGCGGAAACA | (SEQ ID NO: 46) |
| Nkx2.5 | Forward | ACCTCAACAGCTCCCTGACTCT | (SEQ ID NO: 47) |
| | Reverse | ATAATCGCCGCCACAAACTCTCC | (SEQ ID NO: 48) |
| cTnT | Forward | TTCACCAAAGATCTGCTCCTCGCT | (SEQ ID NO: 49) |
| | Reverse | TTATTACTGGTGTGGAGTGGGTGTGG | (SEQ ID NO: 50) |
| β-actin | Forward | TTTGAATGATGAGCCTTCGTCCCC | (SEQ ID NO: 51) |
| | Reverse | GGTCTCAAGTCAGTGTACAGGTAAGC | (SEQ ID NO: 52) |

Annexin V Apoptosis Assay

For FCV progenitor cells, after 2 days differentiation of purified Flk1+ cells on OP9 cells without PKH67 labeling, harvested and stained cells with Abs for PE-conjugated AVAS12 and biotinylated CXCR4. GFP$^+$ cardiomyocytes were purified by FACS at Flk-d6. Then, following staining protocol of the kit, we added Annexin V-FITC, incubated 15 min at room temperature in the dark and subjected to FACS analysis.

EdU Cell Prolifiration Assay

We added EdU solution (Invitrogen) (10 uM) to culture medium 2 hours before sorting FCV cells by FACS, plated sorted FCV cells onto slide by Cytospin (Thermo Shandon) (Waltham, Mass.), fixed by 4% PFA and detected EdU by incubating with Click-iT™ reaction cocktail according to manufacturer direction. To quantify the numbers of EdU$^+$/DAPI$^+$ FCV cells, cells were counted in 10 randomly selected fields. For GFP$^+$ cardiomyocytes, we added EdU solution to culture medium 2 hours before fix at Flk-d3. cTnT$^+$/EdU$^+$/DAPI$^+$ nuclei were counted.

Single Cell Culture

Single sorted FCV cells were plated on OP9 in individual wells of 96-well plates unsing Cloncyte (Beckton Dickinson, Franklin Lakes, N.J.) (Yamashita, J. K. et al. *FASEB J.* 19, 1534-1536 (2005)). After 4 days, triple staining was performed with 1$^{st}$ Abs for Calponin (1:500) from Abcam (Cambridge, UK), cTnT (1:2000) and CD31 (1:200) followed by addition of Alexa488-conjugated anti-rat Ig, Alexa546-conjugated anti-mouse Ig, and APC-conjugated anti-Rabbit 1 g. APC and DAPI staining were imaged in blue and gray, respectively.

FCV Cells Staining

Sorted FCV cells were plated onto slide with Cytospin (Thermo Shandon) and stained with Abs for AVAS12 (1:2000), Nkx2.5 (1:250) from Santa Cruz Biotechnology (Santa Cruz, Calif.) and islet1 (1:500) from the University of IOWA (IOWA city, Iowa). Anti-mouse, rat and rabbit Ig conjugated with Alexa 488 or 546 were used for 2$^{nd}$ Abs.

Analysis of Induced Endothelial and Blood Cells

Flk1$^+$ cells were cocultured with OP9 for 6 days. Floating cells and attached cells were collected and stained with biotin-conjugated anti-CD45 eBioscience (San Diego, Calif.) or anti-CD31 antibody followed by addition of streptavidin-APC. Stained cells were analyzed with FACS vantage.

Statistical Analysis

The data were processed using StatView software for windows (version 5.0, SAS Institute Inc, Cary, N.C.). Values are reported as means±SD. Comparisons among values for all groups were performed by ANOVA. At least three independent experiments were performed. $p<0.05$ was considered significant.

INDUSTRIAL APPLICABILITY

According to this invention, there is provided technology to effectively induce cadiomyocytes and/or cardiac progenitor cells from ES cells or iPS cells, which technology will be useful for cardiac regeneration, especially for treatment of heart diseases through transplantation of the generated cadiomyocytes and/or cardiac progenitor cells in patients.

This invention is not to be limited in scope by the specific embodiments described herein, which are intended as single illustrations of individual aspects of the invention, and any functional equivalents are within the scope of the invention. Indeed, various modifications of the invention, in addition to those shown and described herein will become apparent to those skilled in the art from the foregoing description. Such modifications are intended to fall within the scope of the appended claims. All cited publications, patents, and patent applications are herein incorporated by reference in their entirety in all ways that are consistent with and support the present disclosure.

The invention claimed is:

1. A method for producing cardiomyocytes and/or cardiac progenitor cells, comprising:
   (1) differentiating an induced pluripotent stem (iPS) cell or embryonic stem (ES) cell into a Flk1-positive (Flk1$^+$) mesoderm cell, and
   (2) culturing the Flk1$^+$ cell in the presence of cyclosporine-A.

2. A method of claim 1, wherein the cardiac progenitor cells have an ability to differentiate into myocardium.

3. A method of claim 1, wherein the cardiac progenitor cells are a Flk1$^+$/CXCR4$^+$/vascular endothelial cadherin$^-$ cell population.

4. A method of claim 1, wherein the cardiomyocytes or cardiac progenitor cells have an ability to integrate a myocardial tissue.

5. A method of claim 1, wherein the iPS cell or ES cell is from a mammal.

6. A method of claim 1, wherein the iPS cell is generated from a somatic cell of a mammal.

7. A method of claim 1, wherein the iPS cell is generated from a somatic cell of a mammal by transduction with genes encoding transcription factors of at least Oct and Sox family members.

8. A method of claim 7, wherein the transcription factors further comprise a Klf family member, or a combination of a Klf family member and a Myc family member.

9. A method of claim 5, wherein the mammal is a human or mouse.

10. A method of claim 7, wherein the iPS cell is generated from a human or mouse somatic cell by transduction with genes encoding transcription factors of at least Oct3/4 and Sox2.

11. A method of claim 10, wherein the transcription factors further comprise Klf4, or Klf4 and c-Myc.

12. A method of claim 6, wherein the somatic cell is from tissues or organs.

13. A method for treating a subject with heart disease, comprising transplanting the cardiomyocytes, cardiac progenitor cells, or mixtures thereof produced by the method of claim 1 to the heart of the subject.

14. A method of claim 13, wherein the subject is a human.

15. A method of claim 13, wherein the heart disease is a heart failure including myocardial infarction or cardiomyopathy.

16. A method of claim 13, wherein the cardiac progenitor cells are transplanted to the heart of the subject.

* * * * *

SEQUENCE LISTING

<160> NUMBER OF SEQ ID NOS: 52

<210> SEQ ID NO 1
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
caccatggcg ggacacctgg cttcag                                          26

<210> SEQ ID NO 2
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
acctcagttt gaatgcatgg gagagc                                          26

<210> SEQ ID NO 3
<211> LENGTH: 31
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 3
caccatgtac aacatgatgg agacggagct g                                      31

<210> SEQ ID NO 4
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tcacatgtgt gagaggggca gtgtgc                                            26

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
caccatggct gtcagtgacg cgctgctccc                                        30

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ttaaaaatgt ctcttcatgt gtaaggcgag                                        30

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
caccatgccc ctcaacgtta gcttcaccaa                                        30

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tcacgcacaa gagttccgta gctgttcaag                                        30

<210> SEQ ID NO 9
<211> LENGTH: 21
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 9
taggatcttc ctgcccacca t                                                 21

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tgaccaggat caccaatcca                                                   20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ggcggtggtg acagtatctt                                                   20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ctcggtgatg tacacgatgc                                                   20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
tctcactatg ggcacagcag                                                   20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gcgatgtctg agtgacagga                                                   20

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 15
caacaacata tcggataaac agg                                              23

<210> SEQ ID NO 16
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
aaagtactgt aaggcagttt caggat                                           26

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
caagtgctct cctgctttcc                                                  20

<210> SEQ ID NO 18
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ggctttgtcc agctccact                                                   19

<210> SEQ ID NO 19
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
atgatggtgg tttacaggct aac                                              23

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
tcgatgcact tcactgccag                                                  20

<210> SEQ ID NO 21
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gagatttctc caacccag                                        18

<210> SEQ ID NO 22
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
tctgactttc ggaggtact                                       19

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
aaagaggctc caggtccaat                                      20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
cctctctgct tgtgtggtca                                      20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
tcagctgcat tgaccagaac                                      20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
aagacggtga agttgatggg                                      20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
ctccaaccta tgcggacaat                                               20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28 cccttcata catcggagaa                                                20

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
tgaagaggga agacataact g                                             21

<210> SEQ ID NO 30
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
agcagcccaa agaagaat                                                 18

<210> SEQ ID NO 31
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
cccattccag cgcttctc                                                 18

<210> SEQ ID NO 32
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
gtaatggtgc tcgggcttc                                                19

<210> SEQ ID NO 33
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
gaggaagaag atgctgatga aga                                           23

<210> SEQ ID NO 34
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
gccactgata tcaaaggtgt ctc                                           23

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
cggagaagac tcggatgaag                                               20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
ggcccttcga ttagaaaacc                                               20

<210> SEQ ID NO 37
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
gctcgtcgtc gacaagggct c                                             21

<210> SEQ ID NO 38
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
caaacatgat ctgggtcatc ttctc                                         25

<210> SEQ ID NO 39
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
aacctggagt ttgtgccagg gttt                                                24

<210> SEQ ID NO 40
<211> LENGTH: 24
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 40
tgaacttcac cttccctcca acca                                                24

<210> SEQ ID NO 41
<211> LENGTH: 26
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 41
cagtggcagt ctcaggttaa gaagga                                              26

<210> SEQ ID NO 42
<211> LENGTH: 21
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 42
cgctactgca ggtgtgagca a                                                   21

<210> SEQ ID NO 43
<211> LENGTH: 28
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 43
actttggaag acagaaccaa attatctc                                            28

<210> SEQ ID NO 44
<211> LENGTH: 17
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 44
tgggcaccat tccacca                                                        17

<210> SEQ ID NO 45
<211> LENGTH: 24
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 45
ttgtacggga tcaaatgcgc caag                                                24

<210> SEQ ID NO 46
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
aggccacaca gcggaaaca                                                19

<210> SEQ ID NO 47
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
acctcaacag ctccctgact ct                                            22

<210> SEQ ID NO 48
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
ataatcgccg ccacaaactc tcc                                           23

<210> SEQ ID NO 49
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
ttcaccaaag atctgctcct cgct                                          24

<210> SEQ ID NO 50
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
ttattactgg tgtggagtgg gtgtgg                                        26

<210> SEQ ID NO 51
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
tttgaatgat gagccttcgt cccc                                          24

```
<210> SEQ ID NO 52
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
ggtctcaagt cagtgtacag gtaagc                                          26
```